United States Patent [19]

Bender et al.

[11] Patent Number: 5,393,788
[45] Date of Patent: Feb. 28, 1995

[54] PHENYLALKYL OXAMIDES

[75] Inventors: Paul E. Bender, Cherry Hill, N.J.; Siegfried B. Christensen, IV, Philadelphia, Pa.; Klaus M. Esser, Downingtown, Pa.; Cornelia J. Forster, Bensalem, Pa.; Michael D. Ryan, Pottstown, Pa.; Philip L. Simon, Randolph, N.J.

[73] Assignee: SmithKline Beecham Corporation, Philadelphia, Pa.

[21] Appl. No.: 961,716

[22] PCT Filed: Jul. 8, 1991

[86] PCT No.: PCT/US91/04795
§ 371 Date: Mar. 2, 1993
§ 102(e) Date: Mar. 2, 1993

[87] PCT Pub. No.: WO92/00968
PCT Pub. Date: Jan. 23, 1992

[51] Int. Cl.$^6$ ............... A61K 31/165; C07C 233/00
[52] U.S. Cl. ................... 514/616; 564/155; 564/156

[58] Field of Search ............. 514/231.5, 237.8, 256, 514/337, 352, 357, 397, 398, 399, 406, 471, 541, 616; 544/152, 162, 163, 164, 165, 168, 170, 171, 172, 173, 174, 322, 333, 242, 335; 546/252, 262, 263, 265, 283, 306, 309, 330, 335; 548/315.4, 331.5, 335.5, 338.1, 356.1, 364.1, 372.5; 549/496; 560/12, 13, 16, 39, 41, 42; 562/430, 444; 564/149, 151, 152, 154, 155, 162, 163, 164, 192, 196, 200, 156

[56] References Cited

FOREIGN PATENT DOCUMENTS 51225715  9/1971  Switzerland .
587244  4/1947  United Kingdom .

OTHER PUBLICATIONS

Saijo et al. Chem. Abstract, 112(9) #76634m, 1989.
Ferrand, et al, Chem Abstracts, 99 (25) #195011d, 1983.
Chem Abstracts, 66(7) 28632u, 1967.

Primary Examiner—John M. Ford
Assistant Examiner—Y. N. Gupta
Attorney, Agent, or Firm—James M. Kanagy; Stuart R. Suter; Edward T. Lentz

[57] ABSTRACT

Novel oxamide derivatives are described which inhibit the production of TNF and are useful in the treatment of disease states mediated or exacerbated by TNF production. The compounds of the present invention are also useful as inhibitors of PDE IV and are therefor useful in the treatment of disease states mediated or exacerbated thereby.

3 Claims, No Drawings

PHENYLALKYL OXAMIDES

FIELD OF INVENTION

The present invention relates to novel oxamide derivatives, pharmaceutical compositions containing these compounds and their use in treating allergic and inflammatory diseases and for inhibiting the production of Tumor Necrosis Factor (TNF).

BACKGROUND OF THE INVENTION

Bronchial asthma is a complex, multifactorial disease characterized by reversible narrowing of the airway and hyperreactivity of the respiratory tract to external stimuli.

Identification of novel therapeutic agents for asthma is made difficult by the fact that multiple mediators are responsible for the development of the disease. Thus, it seems unlikely that eliminating the effects of a single mediator will have a substantial effect on all three components of chronic asthma. An alternative to the "mediator approach" is to regulate the activity of the cells responsible for the pathophysiology of the disease.

One such way is by elevating levels of cAMP (adenosine cyclic 3',5'-monophosphate). Cyclic AMP has been shown to be a second messenger mediating the biologic responses to a wide range of hormones, neurotransmitters and drugs; Krebs Endocrinology Proceedings of the 4th International Congress Excerpta Medica, pgs 17-29, 1973). When the appropriate agonist binds to specific cell surface receptors, adenylate cyclase is activated which converts $Mg^{+2}$-ATP to cAMP at an accelerated rate.

Cyclic AMP modulates the activity of most, if not all, of the cells that contribute to the pathophysiology of extrinsic (allergic) asthma. As such, an elevation of cAMP would produce beneficial effects including: 1) airway smooth muscle relaxation, 2) inhibition of mast cell mediator release, 3) suppression of neutrophil degranulation, 4) inhibition of basophil degranulation, and 5) inhibition of monocyte and macrophage activation. Hence, compounds that activate adenylate cyclase or inhibit PDE should be effective in suppressing the inappropriate activation of airway smooth muscle and a wide variety of inflammatory cells. The principal cellular mechanism for the inactivation of cAMP is hydrolysis of the 3'-phosphodiester bond by one or more of a family of isozymes referred to as cyclic nucleotide phosphodiesterases (PDEs).

It has now been shown that a distinct cyclic nucleotide phosphodiesterase (PDE) isozyme, PDE IV, is responsible for cyclic AMP breakdown in airway smooth muscle and inflammatory cells. (Torphy, "Phosphodiesterase Isozymes:Potential Targets for Novel Anti-asthmatic Agents" in New Drugs for Asthma, Barnes, ed. IBC Technical Services Ltd. (1989)). Research indicates that inhibition of this enzyme not only produces airway smooth muscle relaxation, but also suppresses degranulation of mast cells, basophils and neutrophils along with inhibiting the activation of monocytes and neutrophils. Moreover, the beneficial effects of PDE IV inhibitors are markedly potentiated when adenylate cyclase activity of target cells is elevated by appropriate hormones or autocoids, as would be the case in vivo. Thus PDE IV inhibitors would be effective in the asthmatic lung, where levels of prostaglandin E$_2$ and prostacyclin (activators of adenylate cyclase) are elevated. Such compounds would offer a unique approach toward the pharmacotherapy of bronchial asthma and possess significant therapeutic advantages over agents currently on the market.

The compounds of this invention also inhibit the in vivo production of Tumor Necrosis Factor (TNF), a serum glycoprotein. Excessive or unregulated TNF production is implicated in mediating or exacerbating a number of diseases including rheumatoid arthritis, rheumatoid spondylitis, osteoarthritis, gouty arthritis and other arthritic conditions; sepsis, septic shock, endotoxic shock, gram negative sepsis, toxic shock syndrome, adult respiratory distress syndrome, cerebral malaria, chronic pulmonary inflammatory disease, silicosis, pulmonary sarcoisosis, bone resorption diseases, reperfusion injury, graft vs. host reaction, allograft rejections, fever and myalgias due to infection, such as influenza, cachexia secondary to infection or malignancy, cachexia, secondary to acquired immune deficiency syndrome (AIDS), AIDS, ARC (AIDS related complex), keloid formation, scar tissue formation, Crohn's disease, ulcerative colitis, or pyresis.

AIDS results from the infection of T lymphocytes with Human Immunodeficiency Virus (HIV). At least three types or strains of HIV have been identified, i.e., HIV-1, HIV-2 and HIV-3. As a consequence of HIV infection, T-cell mediated immunity is impaired and infected individuals manifest severe opportunistic infections and/or unusual neoplasms. HIV entry into the T lymphocyte requires T lymphocyte activation. Other viruses, such as HIV-1, HIV-2 infect T lymphocytes after T Cell activation and such virus protein expression and/or replication is mediated or maintained by such T cell activation. Once an activated T lymphocyte is infected with HIV, the T lymphocyte must continue to be maintained in an activated state to permit HIV gene expression and/or HIV replication. Monokines, specifically TNF, are implicated in activated T-cell mediated HIV protein expression and/or virus replication by playing a role in maintaining T lymphocyte activation. Therefore, interference with monokine activity such as by inhibition of monokine production, notably TNF, in an HIV-infected individual aids in limiting the maintenance of T cell activation, thereby reducing the progression of HIV infectivity to previously uninfected cells which results in a slowing or elimination of the progression of immune dysfunction caused by HIV infection. Monocytes, macrophages, and related cells, such as kupffer and glial cells, have also been implicated in maintenance of the HIV infection. These cells, like T-cells, are targets for viral replication and the level of viral replication is dependent upon the activation state of the cells. [See Rosenberg et al., The Immunopathogenesis of HIV Infection, Advances in Immunology, Vol. 57, (1989)]. Monokines, such as TNF, have been shown to activate HIV replication in monocytes and/or macrophages [See Poli, et al., Proc. Natl. Acad. Sci., 87:782-784 (1990)], therefore, inhibition of monokine production or activity aids in limiting HIV progression as stated above for T-cells.

TNF has also been implicated in various roles with other viral infections, such as the cytomegalia virus (CMV), influenza virus, and the herpes virus for similar reasons as those noted.

The ability to control the adverse effects of TNF is furthered by the use of the compounds which inhibit TNF in mammals who are in need of such use. There remains a need for compounds which are useful in treating TNF mediated disease states which are exacerbated or caused by the excessive and/or unregulated production of TNF.

SUMMARY OF THE INVENTION

This invention relates to the novel compounds of Formula (1), as shown below, and pharmaceutical compositions comprising a compound of Formula (1), or pharmaceutically acceptable salt thereof, and a pharmaceutically acceptable carrier or diluent.

This invention also relates to a method of inhibiting TNF production in a mammal, including humans, which process comprises administering to a mammal in need of such treatment an effective TNF inhibiting amount of a compound of Formula (1). This method may be used for the prophylactic treatment or prevention of certain TNF mediated disease states amenable thereto.

This invention also relates to a method of treating a human afflicted with a human immunodeficiency virus (HIV), which comprises administering to such human an effective TNF inhibiting amount of a compound of Formula (1).

The compounds of Formula (1) are also useful in the treatment of additional viral infections, where such viruses are sensitive to upregulation by TNF or will elicit TNF production in vivo. The viruses contemplated for treatment herein are those which are sensitive to inhibition, such as by decreased replication, directly or indirectly, by the TNF inhibitors of Formula (1). Such viruses include, but are not limited to; HIV-1, HIV-2 and HIV-3 as noted above, Cytomegalovirus (CMV), Influenza, and Herpes Simplex.

This invention also relates to a method of inhibiting phosphodiesterase IV in an animal, including humans, which comprises administering to an animal in need thereof an effective mount of a compound of Formula (1a), as shown below.

The invention further provides a method for the treatment of allergic and inflammatory disease which comprises administering to a subject in need thereof, an effective mount of a compound of Formula (1a).

The invention also provides a method for the treatment of asthma which comprises administering to a subject in need thereof, an effective amount of a compound of Formula (1a).

DETAILED DESCRIPTION OF THE INVENTION

The compounds of this invention useful in treating a TNF mediated disease by inhibition or reduction of the in vivo levels of TNF are represented by the structure:

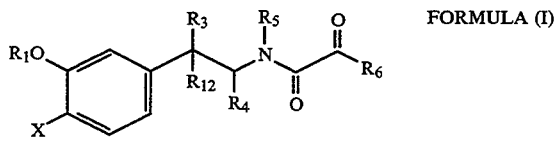

FORMULA (I)

wherein:
$R_1$ is $C_4$–$C_6$ cyclic alkyl, optionally substituted by one to three methyl groups or one ethyl group; $C_{1-7}$ alkyl optionally substituted by 1 or more halogens, —$(CH_2)_nCOO$—$(CH_2)_mCH_3$, $(CH_2)_nO(CH_2)_mCH_3$, $(CH_2)_pOH$, —$CH_2C_5H_9$, $CH_2$—$C_3H_5$, —$C_5H_9$, or

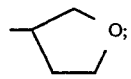

n is 2 to 4;
m is 0 to 2;
p is 2 to 4;
X is $YR_2$, halogen, nitro, amino, $C_{1-2}$ dialkylamine, $C_{1-2}$ monoalkylamine, or formyl amine;
Y is O or $S(O)_{m'}$;
m' is 0 to 2;
$R_2$ is —$CH_3$ or —$CH_2CH_3$ optionally substituted by 1 or more halogens;
$R_3$ is H, $OR_7$ wherein $R_7$ as alkyl can be optionally substituted by 1 or more fluorines, CN, F, $C_{1-2}$ alkyl, $C_{1-2}$ alkyl substituted by 1 or more fluorines, $C(O)OR_7$, $CH_2NR_7R_8$, $CH_2OR_7$, $C(O)NR_7R_8$, or $CH_2NR_7C(O)C(O)NR_7R_8$; provided that when $R_3$ is OH then $R_{12}$ is hydrogen or $CH_3$;
$R_4$ is H, F, CN, $C_{1-2}$ alkyl optionally substituted by 1 or more fluorines, $C(O)NR_7R_8$, $C(O)OR_7$;
$R_{12}$ is hydrogen, F, CN, or —$CH_3$ optionally substituted by 1 to 3 fluorines or $R_3$ and $R_{12}$ together can form a (=O) keto moiety;
$R_5$ is H, $OR_7$, optionally substituted —$(CH_2)_mAr$, or optionally substituted $C_{1-6}$ alkyl;
Ar is 2-, 3- or 4-pyridyl, pyrimidyl, pyridazyl, 2-imidazolyl, morpholino, or phenyl;
$R_6$ is $OR_8$, $NR_7OR_7$, $NR_7$-$NR_7R_8$, $NR_7R_8$, —$OCH_2$-$NR_7C(O)R_{11}$, —$OCH_2C(O)NR_9R_{10}$, —$OCH(R_7)$—$OC(O)C_{1-4}$ alkyl, —$OCH(R_7)$—$C(O)OC_{1-3}$ alkyl;

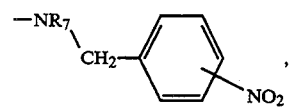

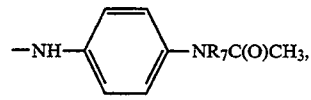

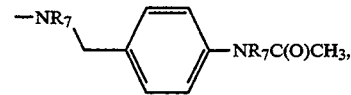

or

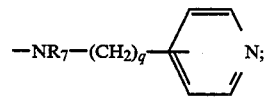

$R_7$ is hydrogen, or $C_{1-3}$ alkyl;
$R_8$ is hydrogen, $C_{1-3}$ alkyl or aryl;
$R_9$ is hydrogen, $CH_3$, $CH_2CH_3$, or $CH_2CH_2OH$;
$R_{10}$ is hydrogen, $CH_3$, $CH_2CH_3$, $CH_2CH_2OH$, or $CH_2CONH_2$;
$R_{11}$ is $CH_3$ or phenyl; and
q is 0 or 1;

provided that $R_1$ is not $C_{2-4}$ alkyl when $R_6$ is OH or $OCH_3$, X is $YR_2$, and $R_2$ is $CH_3$ or $CH_2CH_3$, and Y is oxygen; and pharmaceutically acceptable salts thereof.

This invention also relates to use of the novel compounds of Formula (1a) for inhibition of phosphodiesterase IV, which method comprises administering to an animal, including humans, in need thereof, an effective PDE IV inhibiting amount of a compound of Formula (1a).

The compounds of Formula (1a), readily recognizable as a subgenus of the compounds of Formula (1) are represented by the structure:

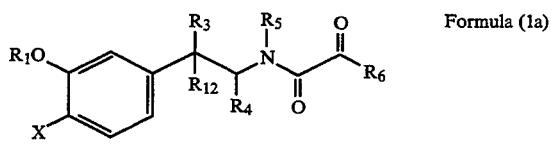

Formula (1a)

wherein:

$R_1$ is $C_4-C_6$ cyclic alkyl, optionally substituted by one to three methyl groups, or one ethyl group; $C_{1-4}$ alkyl substituted by 1 or more fluorines, $C_{2-7}$ alkyl, $(CH_2)_nO(CH_2)_mCH_3$, $-(CH_2)_nCOO(CH_2)_mCH_3$, $-CH_2C_5H_9$, $CH_2-C_3H_5$, or

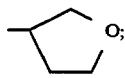

n is 2 to 4;
m is 0 to 2;
X is $YR_2$;
Y is O or $S(O)_{m'}$;
m' is 0 to 2;
$R_2$ is $-CH_3$ or $-CH_2CH_3$ optionally substituted by 1 or more fluorines;
$R_3$ is selected from H, $OR_7$ wherein $R_7$ as alkyl may be optionally substituted by 1 or more fluorines, CN, F, $C_{1-2}$ alkyl optionally substituted by 1 or more fluorines; $C(O)OR_7$, $CH_2NR_7R_8$, $CH_2OR_7$, $C(O)NR_7R_8$ or $CH_2NHC(O)C(O)NR_7R_8$; provided that when $R_3$ is OH then $R_{12}$ is hydrogen or methyl;
$R_{12}$ is hydrogen, F, CN, or $-CH_3$ optionally substituted by 1 to 3 fluorines; or $R_3$ and $R_{12}$ together may form a (=O) keto moiety;
$R_4$ is H, $C_{1-2}$ alkyl optionally substituted by 1 or more fluorines, CN, $C(O)NR_7R_8$, $C(O)OR_7$;
$R_5$ is H, $OR_7$, optionally substituted $C_{1-6}$ alkyl or optionally substituted $-(CH_2)_mAr$;
Ar is 2-, 3- or 4-pyridyl, pyrimidyl, pyridazyl, 2-imidazolyl, morpholino, or phenyl;
$R_6$ is $OR_7$, $NR_7OR_7$, $NR_7R_8$, $NR_7-NR_7R_8$, $-OCH_2-NR_7C(O)R_{11}$, $-OCH_2C(O)NR_9R_{10}$, $-OCH(R_7)-OC(O)C_{1-4}$ alkyl, $-OCH(R_7)-C(O)OC_{1-3}$ alkyl,

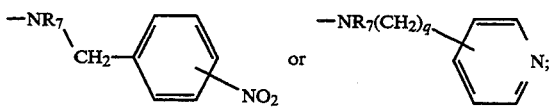

$R_7$ and $R_8$ are independently hydrogen, or $C_{1-3}$ alkyl;
$R_9$ is hydrogen, $CH_3$, $-CH_2CH_3$, or $-CH_2CH_2OH$;

$R_{10}$ is hydrogen, $CH_3CH_2CH_3$, $CH_2CH_2OH$, or $CH_2CONH_2$;
$R_{11}$ is $CH_3$ or phenyl; and
q is 0 or 1;

provided that $R_1$ is not $C_{2-4}$ alkyl when $R_6$ is OH or $OCH_3$, X is $YR_2$, $R_2$ is $CH_3$ or $CH_2CH_3$, and Y is oxygen; and pharmaceutically acceptable salts thereof.

Also included are the pharmaceutically acceptable salt complexes of those compounds of Formulas (1) and (1a) which can form salts.

Preferred optional subtituents for the $R_5$ term of both Formulas (1) and (1a) compounds for the $-(CH_2)_mAr$ and $C_{1-6}$ alkyl groups are substituents selected from hydrogen, $-CH_2(CH_2)_t-NR_7C(O)CH_3$, wherein t is 0 to 5; F, Br, Cl, $C_{1-4}$ alkoxy, $NO_2$, CN, $-NR_7R_8$, $CO_2R_7$, $OR_7$, $C(O)NR_7R_8$, $C(S)NR_7R_8$, $-NR_7C(=NCN)-S-(C_{1-3}$ alkyl), $-NR_7C(=NC-N)-NR_7R_8$, $-NR_7C(O)NR_7R_8$, $-NR_7C(O)C(O)-NR_7R_8$, $-C(=NR_7)-NR_7R_8$, $-S(O)_mCH_3$, $-C(=NR_7)-S(C_{1-3}$ alkyl), $NR_7-S(O)_2-(C_{1-3}alkyl)$, $-OC(O)-R_7$, $-OC(O)-NR_7R_8$, $NR_7S(O)_2CF_3$, $-NR_7C(O)C(O)-OR_7$, $-NR_7C(O)R_7$, $-NR_7-C(O)OR_7$,

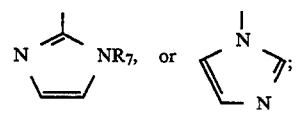

Alternatively the $R_7R_8$ substituents in the $NR_7R_8$ moiety can cyclize to form a 5 or 6 membered ring which may optionally contain some unsaturation and/or contain an additional heteroatom selected from oxygen, nitrogen, or sulfur.

Preferred $R_5$ groups for both Formula (1) and (1a) compounds are H, OH, $CH_3$, $-CH_2-(NHC(O)CH_3)-C_6H_4$), or $-[(NHAc)]-C_6H_4$); prefereably the NHAc moiety is substituted in the para position of the phenyl ring; and $R_7$ as hydrogen. When $R_5$ is $OR_7$, $R_7$ is a lower alkyl of 1 to 10 carbon atoms.

Preferred alkyl groups when the $R_6$ term is $-OCH(R_7)-OC(O)C_{1-4}$ alkyl is t-butyl and when $R_6$ is $-OCH(R_7)-C(O)OC_{1-3}$ alkyl, it is $CH_3$, or $CH_2CH_3$ respectively. Preferred $R_6$ groups for both Formula (1) and (1a) are $-NH_2$, $-OH$, $-OCH_3$, $-NHOH$, $-NHNH_2$,

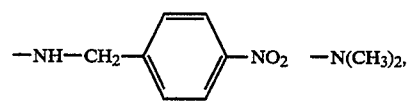

or $-NH(CH_2)_q-$(2, 3, or 4-pyridyl).

Alternatively for $R_6$ moiety the $R_7R_8$ and $R_9R_{10}$ terms in the $NR_7R_8$, and $NR_9R_{10}$ groups repectively, may also cyclize to form a 5 or 6 membered ring which may optionally contain some unsaturation and/or contain an additional heteroatom selected from oxygen, nitrogen, or sulfur.

Preferred $R_3$ substitutions are fluorine, cyano, $C_{1-2}$ alkyl optionally substituted by 1 or more fluorines. Preferred fluorine substituted alkyl groups are $-CF_3$, $-CHF_2$, $-CF_2CHF_2$ or $-CH_2CHF_2$. When $R_3$ is $OR_7$ the $R_7$ term is prefereably hydrogen, and when $R_3$ or $R_4$ is $C(O)OR_7$, $R_7$ is preferably 1-2 carbons.

Preferred R$_4$ substitution for both Formula (1) and (1a) compounds are hydrogen, CN, or C$_{1-2}$ alkyl optionally substitued by 1 or more fluorine. The Ar ring for both Formula (1) and (1a) compounds is preferably substituted in the para position. Preferred Ar groups are phenyl or a 2-, 3-, or 4-pyridyl.

When R$_1$ for the compounds of both Formula (1) and (1a) is a C$_{1-7}$ alkyl substituted by 1 or more halogens, the halogens are preferably fluorine and chlorine, more preferably a C$_{1-4}$ alkyl substituted by 1 or more fluorine, more preferably 1 to 3 times by fluorine. The most preferred chain length is one or two carbons, and most preferred is a —CF$_3$, —CHF$_2$, —CF$_2$CHF$_2$ or —CH$_2$CHF$_2$ moiety. More preferred are those compounds in which R$_1$ is cyclopentyl, —CHF$_2$, or CH$_3$. Most preferred are those compounds in which R$_1$ is cyclopentyl.

When R$_2$ for the compounds of both Formula (1) and (1a) is a C$_{1-2}$ alkyl substituted by 1 or more halogens, the halogens are preferably fluorine and chlorine, more preferably substituted 1 or more times by fluorine, more preferably 1 to 3 times by fluorine. More preferred is a —CF$_3$, CHF$_2$, CF$_2$CHF$_2$ or —CH$_2$CHF$_2$ moiety. Most preferred is a CHF$_2$ moiety.

Preferred X groups for both Formulas (1) and (1a) are those wherein X is YR$_2$, Y is oxygen, and R$_2$ is methyl, or fluoro-substituted alkyl, specifically a C$_{1-2}$ alkyl, such as a —CF$_3$, CHF$_2$, or —CH$_2$CHF$_2$ moiety. For those compounds of Formula (1) wherein the R$_2$ moiety is substituted by 1 or more halogens, the halogens are preferably fluorine and chlorine.

Preferred compounds of both Formula (1) and (1a) are where R$_1$ is cyclopentyl, methyl or CHF$_2$, CF$_3$, —CH$_2$CHF$_2$ or —CF$_2$CHF$_2$; R$_2$ is methyl, CH$_2$F, CHF$_2$, CF$_3$, —CH$_2$CHF$_2$ or —CF$_2$CHF$_2$; X is YR$_2$; R$_4$ is hydrogen or CH$_3$; R$_3$ is hydrogen, CH$_3$, fluoro substituted C$_{1-2}$ alkyl; C(O)OCH$_3$, C(O)OCH$_2$CH$_3$, CONH$_2$, CH$_2$OH, F or CN; R$_{12}$ is hydrogen, methyl, F, or CN; R$_5$ is H, OH, CH$_3$,

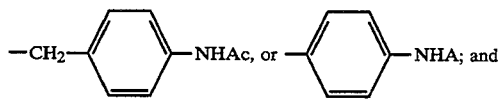

and R$_6$ is —NH$_2$, —OH, —OCH$_3$, —NHOH, —NHNH$_2$, —N(CH$_3$)$_2$,

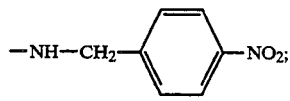

or —NH(CH$_2$)$_q$—(2, 3, or 4-pyridyl).

More preferred are the compounds of Formula (1) and (1a) wherein R$_1$ is cyclopentyl or CHF$_2$, R$_2$ is methyl or CHF$_2$; Y is oxygen; R$_3$ is H, CN or methyl; R$_4$ is hydrogen; R$_{12}$ is hydrogen or methyl; R$_5$ is hydrogen or methyl; and R$_6$ is —NH$_2$, OH, —OCH$_3$ or —NHOH.

The compounds of Formula (1) when R$_1$ is a C$_{2-4}$ alkyl and R$_6$ is OH or OCH$_3$, X is YR$_2$, and R$_2$ is CH$_3$ or CH$_2$CH$_3$, and Y is oxygen are also useful as TNF inhibitors and in the treatment of disease states therein. This subgenus of compounds is referred to hereinafter as Formula (1b).

Especially preferred compounds for use as both TNF inhibitors and in inhibiting PDE IV are:
N-[2-(3-Cyclopentyloxy-4-methoxyphenyl)ethyl]oxamide;
N-[2-(3-Cyclopentyloxy-4-methoxyphenyl)propyl]oxamide
N-[2-(3-Cyclopentyloxy-4-methoxyphenyl)-2-methylpropyl]oxamide
N-[2-Cyano-2-(3-cyclopentyloxy-4-methoxyphenyl)ethyl]oxamide;
N-[2-Cyano-2-methyl-2-(3-cyclopentyloxy-4-methoxyphenyl)ethyl]oxamide;
N-[2-(3-Cyclopentyloxy-4-methoxyphenyl)ethyl]-N-methyloxamide
N-[2-(4-Difluromethoxy-3-methoxyphenyl)ethyl]oxamide;
N-[2-(3-Difluromethoxy-4-methoxyphenyl)ethyl]oxamide; and
N-[(2-(3,4-Bis-difluoromethoxyphenyl)ethyl]oxamide.

Another aspect of the present invention is the novel pharmaceutical compositions of Formula (1) which comprises a pharmaceutically acceptable carrier or diluent and a compound of Formula (1) or a pharmaceutically acceptable salt thereof.

The compounds of the present invention may contain one or more asymmetric carbon atoms and may exist in racemic and optically active forms. All of these compounds are contemplated to be within the scope of the present invention.

By the term C$_{1-7}$ "lower alkyl" or "alkyl" groups as used herein is meant to include both straight or branched chain radicals of 1 to 7 carbon atoms, unless the chain length is limited thereto, including, but not limited to methyl, ethyl, n-propyl, isopropyl, n-butyl, sec-butyl, isobutyl, tert-butyl, and the like.

By the term "aryl" as used herein, in any combination, such as "aryloxy", or "arylalkyl", is meant phenyl, or naphthyl.

By the term "halo" as used herein is meant all halogens, i.e., chloro, fluoro, bromo and iodo.

By the term "inhibiting the production of IL-1" or "inhibiting the production of TNF" is meant
a) a decrease of excessive in vivo IL-1 or TNF levels, respectively, in a human to normal levels or below normal levels by inhibition of the in vivo release of IL-1 by all cells, including but not limited to monocytes or macrophages;
b) a down regulation, at the translational or transcription level, of excessive in vivo IL-1 or TNF levels, respectively, in a human to normal levels or below normal levels; or
c) a down regulation, by inhibition of the direct synthesis of IL-1 or TNF levels as a postranslational event.

By the term "TNF mediated disease or disease states" is meant any and all disease states in which TNF plays a role, either by production of TNF itself, or by TNF causing another cytokine to be released, such as but not limited to IL-1, or IL-6. A disease state in which IL-1, for instance is a major component, and whose production or action, is exacerbated or secreted in response to TNF, would therefore be considered a disease state mediated by TNF. As TNF-$\beta$ (also known as lymphotoxin) has close structural homology with TNF-$\alpha$ (also known as cachectin) and since each induces similar biologic responses and binds to the same cellular receptor, both TNF-$\alpha$ and TNF-$\beta$ are inhibited by the compounds of the present invention and thus are herein referred to collectively as "TNF" unless specifically delineated otherwise. Preferably TNF-α is inhibited.

By the term "cytokine" as used herein is meant any secreted polypeptide that affects the functions of other cells, and is a molecule which modulates interactions between cells in the immune or inflammatory response. A cytokine includes, but is not limited to monokines and lymphokines regardless of which cells produce them. For instance, a monokine is generally referred to as being produced and secreted by a mononuclear cell, such as a macrophage and/or monocyte but many other cells produce monokines, such as natural killer cells, fibroblasts, basophils, neutraphils, endothelial cells, brain astrocytes, bone marrow stromal cells, epideral keratinocytes, and β-lymphocytes. Lymphokines are generally referred to as being produced by lymphoctye cells. Examples of cytokines for the present invention include, but are not limited to, Interleukin-1 (IL-1), Interleukin-6 (IL-6), Intefieukin-8 (IL-8), Tumor Necrosis Factor-alpha (TNFα) and Tumor Necrosis Factor beta (TNFβ).

The inhibition of a cytokine, contemplated by the present invention, for use in the treatment of a HIV-infected human, must be a cytokine which is implicated in (a) the initiation and/or maintenance of T cell activation and/or activated T cell-mediated HIV gene expression and/or replication, and/or (b) any cytokine-mediated disease associated problem such as cachexia or muscle degeneration. The cytokine specifically desired to be inhibited is TNF α.

All of the compounds of Formula (1) are useful in the method of inhibiting the production of TNF, preferably by macrophages, monocytes or macrophages and monocytes in a human in need thereof. All of the compounds of Formula (1a) are useful in the method of inhibiting PDE IV and in treatment of disease states mediated thereby.

The preparation of the compounds of Formula (1) can be carried out by one of skill in the art according to the procedures outlined in the Examples, infra. The preparation of any remaining compounds of Formula (1)

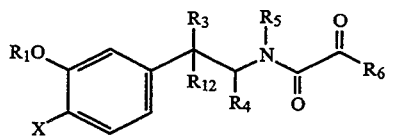

Formula (1)

not described therein may be prepared by the analogous processes disclosed herein, which comprises:

a) for compounds wherein $R_3$ is H, $C_{1-2}$ alkyl optionally substituted by 1 or more fluorines, $R_4$ is H, $CH_3$, CN, or $CO_2R$, $R_5$ and $R_{12}$ are H, reacting a compound of the Formula (2)

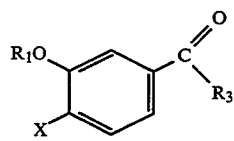

Formula (2)

with nitroalkane, such as nitromethane, in a suitable solvent such as acetic acid with a catalyst at 80°–1015° C. or using conditions described in Shales et al., *J. Amer. Chem. Soc.*, 74, 4486 (1952) to provide a compound of the Formula (3), wherein $R_4$ is CN, H, $CH_3$ or $CO_2R$.

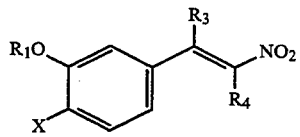

Formula (3)

Reduction with a suitable reductant such as lithium aluminum hydride or hydrogen with a catalyst in the presence of an acid, except where X is SO, $SO_2$ or $NO_2$, Br, I and formyl amine, and suitable modification of the $R_4$ nitrile or ester moiety to yield the amide as taught herein, provides a compound of the Formula (4) wherein $R_3$, $R_4$, and $R_5$ are as defined for Formula (1).

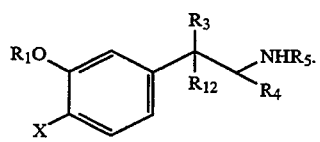

Formula (4)

Compounds of Formula (4) wherein $R_3$, is other than $CH_2NR_7R_8$ or $CH_2NR_7C(O)C(O)NR_7R_8$, unless protected by a group such as t-Butoxycarbonyl or any other easily removed amino protecting groups well known to those skilled in the art; and $R_{12}$, and $R_5$ are as defined for Formula (1) may be further modified, such as by imine formation with an appropriate aldehyde, followed by reduction, and further modification to produce compounds of Formula (4) wherein $R_5$ is other than hydrogen.

Synthesis of compounds of Formula (1) wherein one of $R_3$ is $OR_7$ or F and the other is H or both are F, begins by reaction of a compound of Formula (2) wherein $R_3$ is H with a methyl metal reagent, for example, methyl lithium to provide a compound of Formula (2')

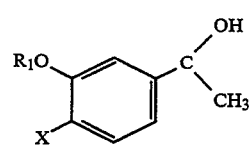

Formula (2')

Oxidation of a compound of Formula 2' with an oxidizing agent, for example pyridium dichromate provides the ketone of Formula (2) as described above wherein $R_3$ is methyl. This compound is treated with a halogenating agent, for example Copper (II) bromide heated in a suitable solvent, to provide the α-halo ketone of Formula (2") wherein X is a halogen, for example bromide.

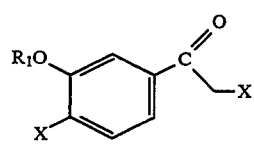

Formula (2")

Displacement of the halogen of Formula (2") by a metal azide, such as sodium azide, in a suitable solvent, such as dimethylformamide provides, the α-azidoketone of Formula (2'''), which is reduced to the corresponding alcohol (Formula 2'''') in one or more steps with hydrogen and a catalyst or an appropriate metal hydride to the Formula (4) compound where $R_3$ is OH, and $R_{12}$, $R_4$ and $R_5$ are H. For example, treatment of the Formula (2''') compound with Na Borohydride provides the Formula (2'''') azido alcohol which is reduced with lithium aluminium hydride to provide the Formula (4) compound. To produce compounds wherein $R_3$ is $OR_7$ the compounds of Formula (2'''') can be alkylated by treatment with a strong base followed by using alkyl-L, as described above, or by using the process of W. Sheppard, Journal of Organic Chemistry, Vol. 29, page 1–15, (1964).

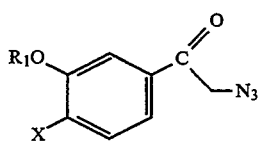

Formula (2''')

Treatment of compounds of Formula (1) where $R_3$ is OH, and $R_{12}$ and $R_4$ are H with an appropriate oxiziding agent, for example, pyridium dichromate in a suitable solvent, such as DMF provides Formula (1) compounds where $R_3$ and $R_{12}$ are together form a keto moiety. Treatment of a Formula (1) compound where $R_3$ is OH or a Formula (2'''') compounds with diethylaminosulfur trifluoride (DAST) provides the corresponding Formula (1) or Formula (2'''') compounds where $R_3$ or $R_{12}$ is F; which provides the corresponding Formula (1) compounds when treated by any of the methods indicated herein.

Treatment of Formula (1) compounds where $R_3$ and $R_{12}$ together form a keto moiety of Formula (2''') or Formula (2'') compounds with DAST provides the corresponding Formula (1), Formula (2''') or Formula (2'''') compounds where $R_3$ and $R_{12}$ are both F; which provides the corresponding Formula (1) compounds when treated by any of the methods indicated herein.

Alternatively, synthesis of some compounds of Formula (1) when X is other than Br, I, $NO_2$, or formylamine, begins by reaction of a compound of the Formula (2) with a lithium halide and a silyl halide in an appropriate solvent followed by reduction with an appropriate reductant, such as a siloxane, to provide a compound of Formula (5) wherein $X_1$ is halogen.

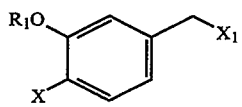

Formula (5)

Halide displacement of a compound of Formula (5) by cyanide provides a compound of Formula (6)'

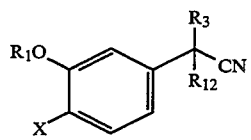

Formula (6)

wherein $R_3$ and $R_{12}$ are H, which is reduced with an appropriate reductant, such as hydrogen with a suitable catalyst, such as nickel with ammonia or palladium on carbon with an acid, such as perchloric acid, to provide a compound of Formula (4), described above, wherein $R_5$ is hydrogen.

Certain compounds of Formula (1) wherein $R_3$ other then $CH_2NR_7R_8$ unless suitably protected, are prepared by reacting a compound of Formula (4) with an appropriately activated oxamic acid derivative of a Formula (7) compound wherein $X_2$ is an activating group, well known to those skilled in the art, such as those disclosed in Bodansky et al., Peptide Synthesis, Wiley & Sons, publishers (1976) pages 99–109. More preferred $X_2$ groups are Cl, Br, $OCH_2CH_3$, $OC(O)CH_3$, $OC(O)CF_3$, $O-C(O)-OCH_2CH_3$, $O-C(O)-OCH_2CH(CH_3)_2$, or $O-C(O)-OCH_2-C_6H_5$ in the presence of a non-nucleophilic base.

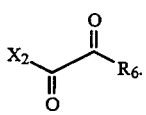

Formula (7)

Alternatively, a compound of Formula (4) is reacted with a suitable alkyl or aryl oxalyl halide, such as methyl oxalyl chloride in the presence of a base; or a mixed anhydride, for example of oxamic acid, or a suitable aryl or alkyl monoester of the formula (7a): $X_3-O-C(O)-C(O)-R_6$, wherein $X_3$ is $R-C(O)-$ or $RO-C(O)-$ and R is alkyl or aryl, and $R_6$ is as defined for Formula (1); or a compound of Formula (8) when using a mixed anhydride of the formula $X_3-C(O)-C(O)-R_{13}$ and $X_3$ is $R-C(O)$ or $RO-C(O)-$, and $R_{13}$ is alkyl or aryl, which is then reacted in the appropriate solvent at elevated temperatures with ammonia, an optionally substituted amine, optionally substituted hydroxylamine, or an optionally substituted hydrazine to produce the compounds of Formula (1).

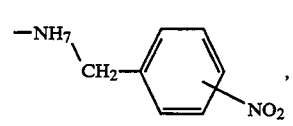

Formula (8)

Alternatively, hydrolysis of the ester, i.e. the $R_{13}$ moiety of a Formula (8) compound to $R_{13}$ as H followed by activation of the acid moiety by a halogenating agent, such as an acid halide oxalyl chloride, or phosphorous oxylchloride, etc.; or a mixed anhydride and reacted with ammonia, an optionally substituted amine, optionally substituted hydroxylamine, or an optionally substituted hydrazine producing the compounds of Formula (1) wherein $R_6$ is $-NR_7R_8$, $-NR_7-NR_7R_8$, $-NR_7OH$, $-NHOH$, $-NHNH_2$,

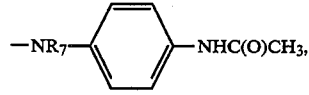

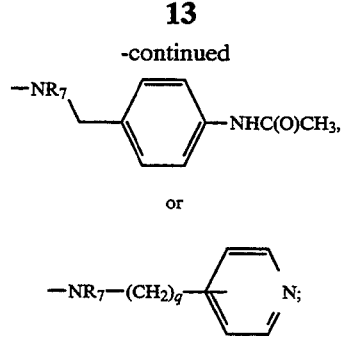

b) or hydrolyzing a compound of Formula (8) as described above, to yield a compound of Formula (8) wherein $R_{13}$ is H, and reacting it ammonia, an optionally substituted amine, optionally substituted hydroxylamine, or an optionally substituted hydrazine and a compound of the formula $R_{14}N=C=NR_{15}$ wherein $R_{14}$ and $R_{15}$ are independently selected from alkyl; cycloalkyl, such as cyclohexyl or dicyclohexyl; alkyl (mono- or dialkyl amino), such as EDAC; aryl or arylalkyl, to produce the compounds of Formula (1) wherein $R_6$ is an amine or substituted amine derivative; or c) for compounds wherein $R_3$ is not H, $CH_2NH_2$ or $CH_2NHC(O)C(O) NH_2$, and X is substituted with other than Br, I, amino, formylamine, and $NO_2$, compounds of Formula (6) wherein $R_3$ and $R_{12}$ are H, are allowed to react with a strong hindered base, such as lithium diisopropylamide (LDA) or hexamethyldisilazylithium (LiHMDS) followed by reaction with an electrophilic reagent bearing $R_3$ other than $CH_2NH_2$ or $CH_2NHC(O)C(O)NH_2$; conversion of Formula (6) where $R_3$ is not hydrogen is then accomplished as described above for Formula (6) where $R_3$ is hydrogen.

A compound of Formula (6) wherein $R_3$ and $R_{12}$ are H; and X is substituted with other than Br, I, amino, formyl amine or $NO_2$; is reacted with a strong hindered base or a metal hydride and then followed by treatment with an appropriately substituted alkyl halo formate or a dialkylcarbonate to produce the corresponding compound of Formula (6) wherein one of $R_3$ or $R_{12}$ is —$CO_2$alkyl; or optionally 2 equivalents are used to produce the corresponding disubstituted —$CO_2$alkyl derivatives of Formula (6); or A compound of Formula (6) wherein one of $R_3$ or $R_{12}$ is alkyl and one of $R_3$ or $R_{12}$ is a —$CO_2$alkyl group is produced by reacting the mono—$CO_2$-alkyl compound produced by the process noted above, with a strong hindered base or a metal hydride followed by treatment with an appropriately substituted alkyl -L wherein L is a leaving group, such as a halide, mesylate or tosylate to produce the desired compound.

Similarly after the Formula (6) compound is treated with the strong base or metal hydride the the resulting anion is treated with hexamethylphosphoramide (HMPA) and an alkyl halide to produce the corresponding compounds wherein one of $R_3$ and $R_{12}$ are alkyl; or optionally using 2 equimolar amounts of HMPA, produce compounds where both $R_3$ and $R_{12}$ are alkyl. Similarly, an analogous method to those described above may be used to obtain Formula (6) intermediates wherein $R_3$ is $CF_3$, and $CHF_2$.

Another process for producing compounds of Formula (1) wherein one of $R_3$ or $R_{12}$ is $CF_3$, $CHF_2$ or $CH_2F$, obtained from the corresponding Formula (2) compounds using the methods described above. The formula (2) compounds where $R_3$ is $CF_3$ are obtained by the method of Shono et al., J. Org. Chem., Vol. 56, pages 2–4 (1991) electrochemically from the Formula (2) compounds where $R_3$ is H.

Formula (2) compounds where $R_3$ is $CF_3$ or $CF_2H$ are obtained by treatment of the Formula 2a compound with a metalling agents at $-78°$ C. followed by the trifluoroacetic acid or difluoro acetic acid by the method of Nad et al., Izvest, (1959) page 71; Chem. Abstr. vol. 53, No. 14977; and Vol. 53, No. 17933 (1959).

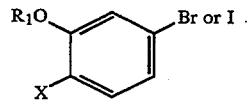

Formula (2a)

Formula (2) compounds where $R_3$ is $CH_2F$ are obtained by treatment of the Formula (2) compounds where $R_3$ is $CH_3$ according to the method of Rozen et al., Synthesis (6) 665, (1985).

Alternatively, a compound of Formula (6) wherein $R_3$ and $R_{12}$ are H; and $R_1$ is as defined above for Formula (1) and X is substituted with other than Br, I, amino, formyl amine or $NO_2$; is reacted with 2 equivalents of a strong hindered base or a metal hydride and 2 equivalents of an appropriately substituted alkyl -L group, wherein L is a leaving group, such as a halide, mesylate or tosylate producing the corresponding compound of Formula (6) wherein $R_3$ and $R_{12}$ are both alkyl.

For a compound of Formula (1) wherein one or both of $R_1$ is —$CF_3$ and X as $YR_2$ is —$OCF_3$ is desired an analogous method is used to that disclosed by W. Sheppard, Journal of Organic Chemistry, Vol. 29, page 1–15, (1964).

d) certain compounds of Formula (1) wherein $R_3$ is $CH_2NR_7R_8$ or $CH_2NR_7C(O)C(O)NR_7R_8$ are prepared by reaction of compounds of Formula (6) wherein $R_3$ is H with a strong hindered base, such as LDA or LiHMDS followed by reaction with, e.g. trimethylsilylisocyanate, and appropriate workup providing compounds of Formula (6) wherein $R_3$ is $CONR_7R_8$. Reduction of the nitrile, (Formula (6)) as described above, followed by protection of the resultant amine with e.g., a t-butylcarbonyl (BOC) group, produces a compound of Formula (4) wherein $R_3$ is $COR_7R_8$ and the amine is protected.

Further reduction of the $R_3$ as $CONH_2$ group, or dehydration of $R_3$ as $CONH_2$ to a nitrile followed by reduction, and then reaction as described above with an appropriate compound of Formula (7) with removal of the BOC protecting group provides for compounds of Formula (1) wherein $R_3$ is $CH_2NH_2$. Further reaction of these compounds of Formula (1) with a compound of Formula (7) in the presence of a nonnucleophilic base, as also described above, yields the resultant compounds wherein $R_3$ is a $CH_2NHC(O)C(O)NH_2$ moiety.

Alternatively, compounds of Formula (4) wherein $R_3$ is $CO_2R$ are reacted with ammonium hydroxide or a suitably substituted amine to produce compounds of Formula (4) wherein $R_3$ is $C(O)NH_2$ or $C(O)NR_7R_8$. Additionally the compounds of Formula (4) wherein $R_3$ is $C(O)NH_2$ or $C(O)NR_7R_8$ can be produced from compounds of Formula (6) which are reduced and optionally deprotected.

e) certain compounds of Formula (1) wherein $R_3$ is CN are prepared from a compound of Formula (4), described above, wherein $R_3$ is $CONH_2$, and $R_5$ is BOC. Dehydration of the $CONH_2$ to CN with, e.g. trifluroacetic anhydride, followed by removal of the BOC protecting group and reaction of the liberated amine as described above then provides a compound of Formula (1) wherein $R_3$ is CN.

Compounds wherein both $R_3$ and $R_{12}$ are cyano are prepared in an analogous manner using a compound of Formula (6) and reacting wherein $R_3$ and $R_{12}$ are H with a strong hindered base or a metal hydride followed by treatment with an appropriately substituted alkyl halo formate or a dialkylcarbonate to produce the corresponding compound of Formula (6) wherein one of $R_3$ or $R_{12}$ is $-CO_2$-alkyl; the resulting compound is further reacted by treatment again with either a strong hindered base or a metal hydride and followed by treatment with an appropriately substituted alkyl halo formate or dialkylcarbonate to produce the corresponding disubstituted $-CO_2$alkyl derivatives of Formula (6). The resultant diester moiety is reduced, and protected and the esters are amidated for example, with ammonia either under pressure or in an alcoholic solvent; or alternatively with the trimethylaluminum adduct of ammonia or ammonium chloride in an inert solvent such as methylene chloride or toluene, between ambient temperature and 60° C. under an inert atmosphere, providing a compound of Formula (4) wherein $R_3$ and $R_{12}$ are $CONH_2$ and $R_5$ is BOC. The resultant compound is then dehydrated, such as by using trifluoroacetic anhydride and pyridine in THF, to produce a compound of formula (4) wherein $R_3$ and $R_{12}$ are CN and $R_5$ is BOC. Removal of the BOC protecting group with, for example, trifluoroacetic acid, followed by further reaction of the amine as described above, or with methyl oxalyl chloride, and then with ammonia under pressure provides the compound of Formula (1);

f) compounds wherein $R_4$ is not H, reaction of Formula (2) with an appropriately protected amine provides compounds of Formula (9)

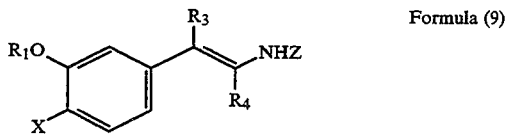

Formula (9)

wherein Z is a suitable protecting group. Such protecting groups are known to those skilled in the art and are readily disclosed in Greene. T., *Protective Groups in Organic Synthesis*, Wiley Publishers, NY (1981), the contents of which are hereby incorporated by reference. The reduction of the double bond and amine deprotection provides a compound of Formula (4) where $R_3$ is hydrogen, which is converted to Formula (1) compounds, as described above.

g) compounds of Formula (1) wherein X is formyl amine are formed at the last step, by formylating a compound wherein X is $NH_2$, obtained by removal of a protecting group from the amine functionality. Such protective groups are well known to those skilled in the art, See Greene, T., Supra.

h) compounds of Formula (1) wherein X is Br or I may be prepared using the techniques of Example 15 on a similarly deprotected amine, diazotization of the amine, and diazonium displacement.

i) compounds of Formula (1) wherein X is $NO_2$ may be prepared using the techniques of Example 15 on a similarly deprotected amine by oxidation of the amine to the nitro group.

j) compound of Formula (1) wherein $R_3$ and $R_{12}$ are other than hydrogen can readily be prepared by one skilled in the art using the techniques illustrated above for R3 as other than hydrogen.

METHODS OF TREATMENT

The compounds of Formula (1) or a pharmaceutically acceptable salt thereof can be used in the manufacture of a medicament for the prophylactic or therapeutic treatment of any disease state in a human, or other mammal, which is exacerbated or caused by TNF production by such human's cell, such as but not limited to monocytes and/or macrophages, especially caused by excessive or unregulated TNF production. The compounds of Formula (1) are administered in an amount sufficient to inhibit TNF production such that it is regulated down to normal levels, or in some case to subnormal levels, so as to ameliorate or prevent the disease state. Abnormal levels of TNF, for the present invention, constitute levels of 1) free (not cell bound) TNF, greater than or equal to 1 picogram per ml; 2) any cell associated TNF; or 3) the presence of TNF mRNA above basal levels in cells or tissues in which TNF is produced.

The compounds of Formula (1a), or a pharmaceutically acceptable salt thereof can be used in the manufacture of a medicament for the prophylatic or therapeutic treatment of any disease state, in a human, or other mammal, which is exacerbated or caused by PDE IV, such as but not limited to asthma, allergic or inflammatory diseases. The compounds of Formula (1a) are administered in an amount sufficient to treat such a disease in a human or other mammal.

The compounds of Formula (1) may be used topically as well in the treatment or prophylaxis of inflammatory topical disease states mediated or exacerbated by excessive TNF production respectively, such as rheumatoid arthritis, rheumatoid spondylitis, osteoarthritis, gouty arthritis and other arthritic conditions, inflamed joints, eczema, psoriasis or other inflammatory skin conditions such as sunburn; inflammatory eye conditions including conjunctivitis; pyresis, pain and other conditions associated with inflammation.

It further appears that among the cytokines, while TNF production precedes and augments the function of IL-1 and other cytokines, there is no clear data on how the relationship among these molecules contributes to inflammation-related disease states. The present invention attributes many of the biological disease states attributable to interlekin-1 (IL-1) activity as being attributable to that of TNF activity as well. A comprehensive listing of IL-1 activities can be found in Dinarello, *J. Clinical Immunology*, 5 (5), 287-297 (1985). It should be noted that some of these effects have been described by others as indirect effects of IL-1. The myriad of known biological activities of IL-1 include the activation of T helper cells, induction of fever, stimulation of prostaglandin or collagenase production, neutrophil chemotaxis, induction of acute phase proteins and the suppression of plasma iron levels. These disease states are also considered appropriate disease states of TNF activity and hence compounds of Formula (1) are also useful in their treatment as well, and the use of the compounds of Formula (1) should not be considered solely limited to the specifically described TNF mediated disease states herein. The compounds of Formula (1) should be efficacious in an IL-1 mediated disease state as TNF and IL-1 act in a synergistic manner. TNF as well mediates the release, in some instances, of IL-1, therefore a reduction in the levels of TNF may be useful in the treatment of a disease state wherein IL-1 is a major component. The present invention relates therefore, to an effective, TNF production inhibiting amount of a compound of Formula (1) or a pharmaceutically acceptable salt thereof is useful in treating, prophylactically or therapeutically, any disease state in a human which is exacerbated or caused by excessive or unregulated IL-1 production, i.e., where IL-1 is a major component, by such human's monocytes and/or macrophages.

The method of treatment and monitoring for an HIV-infected human manifesting immune dysfunction or cytokine-mediated disease associated problems is taught in Hanna, WO 90/15534, Dec. 27, 1990. In general, an initial treatment regimen can be copied from that known to be effective in interfering with TNF activity for other TNF mediated disease states by, the compounds of Formula (1). Treated individuals will be regularly checked for T cell numbers and T4/T8 ratios and/or measures of viremia such as levels of reverse transcriptase or viral proteins, and/or for profession of monokinemediated disease associated problems such as cachexia or muscle degeneration. If no effect is seen following the normal treatment regimen, then the amount of the monokine activity interfering agent administered is increased, e.g., by fifty percent per week.

The compounds of Formula (1) may be administered orally (when active by this route), topically, parenterally or by inhalation in conventional dosage forms prepared by combining such agent with standard pharmaceutical carriers according to conventional procedures in an amount sufficient to produce the desired therapeutic activity for treatment of a TNF mediated disease state or in the case of a compound of Formula (1a) in their use as a PDE IV inhibitor.

The pharmaceutical composition of the present invention will comprise an effective, non-toxic amount of a compound of Formula (1) and a pharmaceutically acceptable carrier or diluent. The compounds of Formula (1) and (1a) as used herein, are administered in conventional dosage forms prepared by combining a compound of Formula (1) in an effective amount sufficient to produce the desired activity, respectively, with standard pharmaceutical carriers according to conventional procedures. These procedures may involve mixing, granulating and compressing or dissolving the ingredients as appropriate to the desired preparation.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time delay material well known to the art, such as glyceryl monostearate or glyceryl distearate alone or with a wax.

Compounds of Formula (1) and (1a) and their pharmaceutically acceptable salts can be employed in a wide variety of pharmaceutical forms. The preparation of a pharmaceutically acceptable salt will be determined by the nature of the compound itself, and can be prepared by conventional techniques readily available to one skilled in the art. Thus, if a solid carrier is used, the preparation can be tableted, placed in a hard gelatin capsule in powder or pellet form or in the form of a troche or lozenge. The amount of solid carrier will vary widely but preferably will be from about 25 mg to about 1 gram. When a liquid carrier is used, the preparation will be in the form of a syrup, emulsion, soft gelatin capsule, sterile injectable liquid such as an ampule or nonaqueous liquid suspension. Where the composition is in the form of a capsule, any routine encapsulation is suitable, for example using the aforementioned carriers in a hard gelatin capsule shell. Where the composition is in the form of a soft gelatin shell capsule any pharmaceutical carrier routinely used for preparing dispersions or suspensions may be considered, for example aqueous gums, celluloses, silicates or oils and are incorporated in a soft gelatin capsule shell. A syrup formulation will generally consist of a suspension or solution of the compound or salt in a liquid carrier for example, ethanol, glycerine or water with a flavouring or coloring agent.

The amount of a compound of Formula (1) and (1a) required for therapeutic systemic" administration will, of course, vary with the compound chosen, the nature and severity of the condition, and the mammal, including humans, undergoing treatment, and is ultimately at the discretion of the physician.

The term 'parenteral' as used herein includes intravenous, intramuscular, subcutaneous intranasal, intrarectal, intravaginal or intraperitoneal administration. The subcutaneous and intramuscular forms of parenteral administration are generally preferred. Appropriate dosage forms for such administration may be prepared by conventional techniques. By the term "systemic" administration is meant oral, intravenous, intraperitoneal and intramuscular administration.

Typical parenteral compositions consist of a solution or suspension of the compound or salt in a sterile aqueous or non-aqueous carrier optionally containing a parenterally acceptable oil, for example polyethylene glycol, polyvinylpyrrolidone, lecithin, arachis oil, or sesame oil.

The dally dosage regimen for via parenteral administration is suitably about 0.001 mg/Kg, to 40 mg/Kg, of a compound of the Formula (1) or a pharmaceutically acceptable salt thereof calculated as the free base.

The compounds of Formula (1) and ( 1a) may be administered orally. Each dosage unit for oral administration contains suitably from 1 mg to 100 mg, and preferably from 10 mg to 30 mg of a compound of Formula (I) or a pharmaceutically acceptable salt thereof calculated as the free base.

The daily dosage regimen for oral administration is suitably about 0.01 mg/Kg to 100 mg/Kg, preferably from about 10 mg to about 30 mg/kg, of a compound of Formula 1) and (1a) or a pharmaceutically acceptable salt thereof calculated as the free base. The active ingredient may be administered from 1 to 6 times a day, sufficient to exhibit the desired activity.

The compounds of Formula (1) and (1a) may also be administered by inhalation. By "inhalation" is meant intranasal and oral inhalation administration. Appropriate dosage forms for such administration, such as an aerosol formulation or a metered dose inhaler, may be prepared by conventional techniques. The daily dosage regimen for a compound of Formula (1) for intranasal administration and oral inhalation is suitably about 10 to about 1200 mg.

Typical compositions for inhalation are in the form of a solution, suspension or emulsion that may be administered as a dry powder or in the form of an aerosol using a conventional propellant such as dichlorodifluoromethane or trichlorofluoromethane.

Preferably the composition is in unit dosage form, for example a tablet, capsule or metered aerosol dose, so that the patient may administer to himself a single dose.

The compounds of Formula (1) and (1a) may also be administered topically. By topical administration is meant non-systemic administration and includes the application externally to the epidermis, to the buccal cavity and instillation of such a compound into the ear, eye and nose, and where the compound does not significantly enter the blood stream.

A suitable dose of a TNF production inhibiting compound of Formula (1) is 0.01 mg to about 100 mg of base for topical administration, the most preferred dosage being about 0.01 mg to about 30 mg, for example, 0.003 mg to 10 mg administered two or three times daily.

While it is possible for an active ingredient to be administered alone as the raw chemical, it is preferable to present it as a pharmaceutical formulation. The active ingredient may comprise, for topical administration, from 0.001% to 10% w/w, e.g. from 1% to 2% by weight of the formulation although it may comprise as much as 10% w/w but preferably not in excess of 5% w/w and more preferably from 0.1% to 1% w/w of the formulation.

The topical formulations of the present invention comprise an active ingredient together with one or more acceptable carrier(s) therefor and optionally any other therapeutic ingredient(s). The carrier(s) must be 'acceptable' in the sense of being compatible with the other ingredients of the formulation and not deleterious to the recipient thereof.

Formulations suitable for topical administration include liquid or semi-liquid preparations suitable for penetration through the skin to the site of inflammation such as liniments, lotions, creams, ointments or pastes, and drops suitable for administration to the eye, ear or nose.

It will be recognized by one of skill in the art that the optimal quantity and spacing of individual dosages of a compound of Formula (1) or a pharmaceutically acceptable salt thereof will be determined by the nature and extent of the condition being treated, the form, route and site of administration, and the particular patient being treated, and that such optimums can be determined by conventional techniques. It will also be appreciated by one of skill in the art that the optimal course of treatment, i.e., the number of doses of a compound of Formula (1) or a pharmaceutically acceptable salt thereof given per day for a defined number of days, can be ascertained by those skilled in the art using conventional course of treatment determination tests.

UTILITY EXAMPLES

EXAMPLE A

The inhibitory effect of compounds of Formula (1) on in vitro TNF production by Human Monocytes can be determined by the protocol as described in Badger et al., EPO published Application 0 411 754 A2, Feb. 6, 1991, and in Hanna, WO 90/15534, Dec. 27, 1990. The compounds of Examples 4, 7, 8, 15 to 18, 22 and 24 all displayed an IC50 value of 0.01- to about >3.0 for Inhibition of LPS-Induced Human Monocyte TNF Production in the above noted assay.

UTILITY EXAMPLE B

Two models of endotoxin shock have been utilized to determine in vivo TNF activity for the compounds of Formula (1). The protocol used in these models is described in Badger et al., EPO published Application 0 411 754 A2, Feb. 6, 1991, and in Hanna, WO 90/15534, Dec. 27, 1990. In these models protection from the lethal effects of endotoxin shock is provided by the compound N-[2-(3-Cyclopentyloxy-4-methoxyphenyl)ethyl]oxamide. This showed a reduction in serum TNF levels in the LPS/GAL mouse model of endotoxic shock and inhibition of TNF production in the P acnes/LPS treated mice model. The compound also demonstrated an 80% survival rate of the animals with endotoxic shock in the P acnes/LPS model after treatment with N-[2-(3-Cyclopentyloxy-4-methoxyphenyl)ethyl]oxamide compared to 100% lethality of the animals in a control group.

It has also been determined, using one or both of the in vivo assays described herein, that N-2-(3,4-dimethoxyphenethyl)oxamide also inhibited in vivo TNF levels as well as protected the animals from endotoxic induced shock.

The data shown herein demonstrate that the compounds of the present invention inhibit TNF production in a mammal. Therefore, the compounds of Formula (1) are useful in inhibiting the production of tumor necrosis factor (TNF) by monocytes or macrophages in a human.

UTILITY MODEL C

The phosphodiesterase inhibitory activity and selectivity of the compounds of Formula (1a) can be determined using a battery of five distinct PDE isozymes. The tissues used as sources of the different isozymes are as follows: 1) PDE Ia, canine trachealis; 2) PDE Ib, porcine aorta; 3) PDE Ic, guinea-pig heart; 4) PDE III, guinea-pig heart; and 5) PDE IV, human monocyte. PDEs Ia, Ib, Ic and III are partially purified using standard chromatographic techniques (Torphy and Cieslinski, Mol. Pharmacol. 37:206–214, 1990). PDE IV is purified to kinetic homogeneity by the sequential use of anion-exchange followed by heparin-Sepharose chromatography (White et al., FASEB J. 4:A1987 1990).

UTILITY MODEL D

Phosphodiesterase activity is assayed as described in the protocol of Torphy and Cieslinski, Mol. Pharmacol. 37:206–214, 1990. $IC_{50}$'s for compounds of Formula (1a) range from 0.05 $\mu$M to 40 $\mu$M.

UTILITY MODEL E

The ability of selected PDE IV inhibitors to increase cAMP accumulation in intact tissues is assessed using U-937 cells, a human monocyte cell line that has been shown to contain a large amount of PDE IV. To assess the activity of PDE IV inhibition in intact cells, nondifferentiated U-937 cells (approximately $10^5$ cells/reaction tube) were incubated with various concentrations (0.01–100 $\mu$M) of PDE inhibitors for one minute and 1 $\mu$M prostaglandin E2 for an additional four minutes. Five minutes after initiating the reaction, cells were lysed by the addition of 17.5% perchloric acid, the pH was neutralized by the addition of 1M potassium carbonate and cAMP content was assessed by RIA. A general protocol for this assay is described in Brooker et al., Radioimmunoassay of cyclic AMP and cyclic GMP., Adv. Cyclic Nucleotide Res., 10:1–33, 1979. EC$_{50}$'s for compounds of Formula (1a) range from 0.5 μM to >10 μM.

SYNTHETIC EXAMPLES

The following examples are illustrative and are not limiting of the compounds of this invention.

EXAMPLE 1

3-Cyclopentyloxy-4-methoxy-β-nitrostyrene a) 3-Cyclopentyloxy-4-methoxybenzaldehyde. A mixture of 3-hydroxy-4-methoxybenzaldehyde (40 g, 0.26 mol), potassium carbonate (40 g, 0.29 mol) and bromocyclopentane (32 mL, 0.31 mol) in dimethylformamide (0.25 L) was heated under an argon atmosphere at 100° C. After 4 h, additional bromocyclopentane (8.5 mL, 0.08 mol) was added and heating was continued for 4 h. The mixture was allowed to cool and was filtered. The filtrate was concentrated under reduced pressure and the residue was partitioned between ether and aqueous sodium bicarbonate. The organic extract was washed with aqueous sodium carbonate and dried (potassium carbonate). The solvent was removed in vacuo and the residue was purified by flash chromatography, eluting with 2:1 hexanes/ether to provide the product (52 g, 89%) as a pale yellow oil. Analysis Calc. for $C_{13}H_{16}O_3$: C 70.89, H 7.32; found: C 70.71, H 7.33.

b) 3-Cyclopentyloxy-4-methoxy-β-nitrostyrene. To a solution of 3-cyclopentyloxy-4-methoxybenzaldehyde (6.04 g, 27.2 mmol) in glacial acetic acid (36 mL) under an argon atmosphere was added nitromethane (7.35 mL, 136.0 mmol) and ammonium acetate (3.15 g, 40.8 mmol). The resulting mixture was heated at reflux for 3 h, then allowed to cool to room temperature. The mixture was poured into water and extracted twice with methylene chloride. The combined organic extracts were washed successively with aqueous sodium bicarbonate and water and dried (potassium carbonate). Removal of the solvent in vacuo and purification of the residue by flash chromatography, eluting with 1:1 methylene chloride/hexanes, provided the nitrostyrene (5.90 g, 82%) as a bright yellow solid: m.p. 133°–134° C.

Analysis Calc. for $C_{14}H_{17}NO_4$: C 63.87, H 6.51, N 5.32; found: C 64.08, H 6.42, N 5.33.

EXAMPLE 2

2-(3-Cyclopentyloxy-4-methoxyphenyl)ethylamine

To a suspension of lithium aluminum hydride (10.83 g, 28.5 mmol) in ether (250 mL) at 0° C. under an argon atmosphere was added dropwise a solution of 3-cyclopentyloxy-4-methoxy-β-nitrostyrene (15.00 g, 57.0 mmol) in tetrahydrofuran (85 mL). The resulting mixture was allowed to warm to room temperature and stirred overnight. The reaction mixture was cooled to 0° C. and quenched by the successive dropwise addition of water (11 mL), 15% sodium hydroxide (11 mL) and water (33 mL). The mixture was filtered through a pad of Celite TM and the filtrate was washed successively with water, 10% hydrochloric acid and water. The aqueous washes were combined, made basic with saturated aqueous potassium carbonate and extracted three times with ether and twice with methylene chloride. The organic layers were combined and dried (potassium carbonate). Removal of the solvent in vacuo provided the amine (10.80 g, 81%). A portion of the crude amine was purified by flash chromatography, eluting with 1:10:90 water/methanol/chloroform.

Analysis Calc. for $C_{14}H_{21}NO_2 \cdot \frac{2}{3} H_2O$: C 68.19, H 9.09, N 5.68; found C 68.39, H 9.16, N 5.85.

EXAMPLE 3

Methyl-N-[2-(3-Cyclopentyloxy-4-methoxyphenyl)ethyl]oxamate

To a solution of 2-(3-cyclopentyloxy-4-methoxyphenyl)ethylamine (884 mg, 3.8 mmol) and triethylamine (0.53 mL, 4.1 mmol) in methylene chloride (4 mL) at 0° C. under an argon atmosphere was added dropwise methyl oxalyl chloride (0.38 mL, 4.1 mmol) and the resulting mixture was stirred for 30 min. The reaction mixture was partitioned between water and methylene chloride and the organic extract was washed with saturated aqueous sodium chloride and dried (sodium sulfate). The solvent was removed in vacuo and the residue was purified by flash chromatography, eluting with 4:6 ethyl acetate/hexanes to provide the oxamate (605 mg, 50%): m.p. 73°–74° C.

Analysis Calc. for $C_{17}H_{23}NO_5$: C 63.54, H 7.21, N 4.36; found C 63.17, H 7.14, N 4.43.

EXAMPLE 4

N-[2-(3-Cyclopentyloxy-4-methoxyphenyl)ethyl]oxamic acid

To a solution of methyl N-[2-(3-cyclopentyloxy-4-methoxy)phenylethyl]oxamate (541 mg, 1.7 mmol) in methanol (7 mL) under an argon atmosphere was added lithium hydroxide monohydrate (212 mg, 5.0 mmol). After stirring at room temperature for 1 h, the mixture was concentrated under reduced pressure. The residue was partitioned between 10% hydrochloric acid and methylene chloride and the organic extract was dried (magnesium sulfate). The solvent was removed in vacuo to provide the acid (482 mg, 93%): m.p. 123°–124° C.

Analysis Calc. for $C_{16}H_{21}NO_5$: C 62.53, H 6.89, N 4.56; found: C 62.27, H 6.78, N 4.52.

EXAMPLE 5

N-[2-(3-Cyclopentyloxy-4-fluorophenyl)ethyl]oxamide a) 2-Fluoro-5-methylphenol 2-Fluoro-5-methylaniline (9.0 mililiters (mL hereinafter), 0.08 mol) was treated with hot 35% sulfuric acid (80 mL), and the resulting mixture was cooled to 15° C. Ice (80 grams (g hereinafter) was added and a solution of sodium nitrite (7.16 g, 0.10 moles (mol hereinafter) in water (70 mL) was added dropwise over 1 hour (h hereinafter), maintaining the temperature at 0° C. After stirring an additional 15 minutes (min hereinafter), urea (1.44 g, 0.024 mol) was added and the mixture was poured into a solution of copper (II) sulfate pentahydrate (310 g, 1.240 mol) in water (2.4 Liters (L hereinafter)), with stirring. To the resulting mixture was added copper (I) oxide (10.4 g, 0.073 mol) and the mixture was stirred vigorously for 30 min. The reaction mixture was extracted with methylene chloride and dried (magnesium sulfate). The solvent was removed in vacuo and the residue was redissolved in methylene chloride, washed with water and dried (magnesium sulfate). Removal of the solvent in vacuo provided the phenol (7.98 g, 79%) which was used without further purification.

b) 3-Cyclopentyloxy-4-fluorotoluene. A solution of 2-fluoro-5-methylphenol (7.91 g, 63 mmol) was used to prepare the title compound by the analogous method of Example 1(a) above yielding (3.01 g, 25%).

c) α-Bromo-3-cyclopentyloxy-4-fluorotoluene. To a solution of 3-cyclopentyloxy-4-fluorotoluene (3.00 g, 15.4 mmol) in carbon tetrachloride (200 mL) under an argon atmosphere was added N-bromosuccinimide (3.63 g, 20.4 mmol) and benzoyl peroxide (catalytic amount). After stirring for 2 h under a 189 W tungsten lamp, the reaction mixture was filtered and the solvent was removed under reduced pressure. The residue was purified by flash chromatography, eluting with 1% ether/hexanes to provide the bromide (3.22 g, 76%).

d) 3-Cyclopentyloxy-4-fluorobenzaldehyde. To a solution of sodium ethoxide, prepared from sodium (215 miligrams (mg hereinafter), 9.15 mmol) in absolute ethanol (15 mL) under an argon atmosphere, was added a solution of α-bromo-3-cyclopentyloxy-4-fluorotoluene (2.52 g, 9.15 mmol) in ethanol (5 mL). 2-Nitropropane (0.86 mL, 9.52 mmol) was added, followed by additional ethanol (5 mL). The resulting mixture was stirred at room temperature for 6 h and filtered. The filtrate was concentrated under reduced pressure and the residue was triturated with ether and filtered. The solvent was removed under reduced pressure and the residue was purified by flash chromatography, eluting with 2.5% ether/hexanes to provide the benzaldehyde (937 mg, 49%).

e) 3-Cyclopentyloxy-4-fluoro-β-nitrostyrene. The title compound was prepared using a solution of 3-cyclopentyloxy-4-fluorobenzaldehyde (857 mg, 4.1 mmol) in an analogous method of Example 1(b) described above, yielding the nitrostyrene (552 mg, 53%): m.p. 90°–91.5° C.

f) 2-(3-Cyclopentyloxy-4-fluorophenylethyl)amine. The title compound was prepared using the analogous method of Example 2 and a solution of 3-cyclopentyloxy-4-fluoro-β-nitrostyrene (490 mg, 1.95 mmol) to provide the amine (287 mg, 66%).

g) N-[2-(3-Cyclopentyloxy-4-fluorophenyl)ethyl]oxamide. To a suspension of oxamic acid (100 mg, 1.1 mmol) in dimethoxyethane (3.5 mL) was added N-methylmorpholine (0.15 mL, 1.3 mmol) followed by ethyl chloroformate (0.13 mL, 1.3 mmol). The resulting mixture was stirred under an argon atmosphere at room temperature for 3 h, at which time a solution of 2-(3-cyclopentyloxy-4-fluorophenylethyl)amine (251 mg, 1.1 mmol) in dimethoxyethane (2.5 mL) was added. After stirring at room temperature overnight, the mixture was concentrated under reduced pressure. The residue was dissolved in 3% methanol/methylene chloride (185 mL) and washed successively with aqueous sodium bicarbonate, water, 10% hydrochloric acid and water and dried (potassium carbonate). The solvent was removed in vacuo and the solid residue was recrystallized from methylene chloride to provide the product (125 mg, 38%): m.p. 183°–184.5° C.

Analysis Calc. for $C_{15}H_{19}FN_2O_3 \cdot \frac{1}{8} H_2O$: C 60.75, H 6.54, N 9.45, F 6.41; found C 60.68, H 6.33, N 9.47, F 6.31.

EXAMPLE 6

N-[2-(3-Cyclopentyloxy-4-chlorophenyl)ethyl]oxamide a) 4-Chloro-3-cyclopentyloxytoluene. Using a solution of 2-chloro-5-methylphenol (14.3 g, 100 mmol) in the analogous method of Example 1(a) above provided the title compound (19.45 g, 92%).

b) α-Bromo-4-chloro-3-cyclopentyloxytoluene. Using a solution of 4-chloro-3-cyclopentyloxytoluene (18.00 g, 85.4 mmol) in an analogous method to Example 5(c) above provided the title compound (16.95 g, 66%).

c) 4-Chloro-3-cyclopentyloxybenzaldehyde. Using a solution α-bromo-4-chloro-3-cyclopentyl-oxytoluene (10.51 g, 36.2 mmol) in an analogous method to Example 5(d) above provided the benzaldehyde (4.36 g, 54%).

d) 4-Chloro-3-cyclopentyloxy-β-nitrostyrene. Using a solution of 4-chloro-3-cyclopentyloxybenzaldehyde (751 mg, 3.3 mmol) in an analogous method to Example 1(b) above provided the nitrostyrene (636 mg, 71%): m.p. 105°–107° C.

e) 2-(4-Chloro-3-cyclopentyloxyphenylethyl)amine. The title compound was produced in an analogous method to that of Example 2 above using 4-chloro-3-cyclopentyloxy-β-nitrostyrene to provided the amine (435 mg, 77%).

f) N-[2-(4-Chloro-3-cyclopentyloxyphenyl)ethyl]oxamide. The title compound was produced in an analogous method to that of Example 5, part g, above using 2-(4-chloro-3-cyclopentyl-oxyphenylethyl)amine to provide the oxamide (139 mg, 32%): m.p. 179°–180° C.

Analysis Calc. for $C_{15}H_{19}ClN_2O_3$: C 57.97, H 6.16, N 9.01, Cl 11.41; found C 57.83, H 6.15, N 8.92, Cl 11.12.

EXAMPLE 7

N-{2-[3-(4-Hydroxybutoxy)-4-methoxyphenyl]ethyl}oxamide a) Ethyl 4-(4-formyl-2-methoxyphenoxy)butanoate. The title compound was produced in an analogous method to that of Example 1(a) using a solution of 4-methoxy-3-hydroxybenzaldehyde (25.0 g, 0.164 mol) and substituting ethyl 4-bromobutanoate (27.5 mL, 0.192 mmol) for cyclopentyl bromide to yield a white solid: m.p. 47°–49° C.

b) Ethyl 4-[2-methoxy-4-(2-nitroethenyl)phenoxy]butanoate. Using ethyl 4-(4-formyl-2-methoxyphenoxy)butanoate (16 g, 60 mmol) in an analogous method to that of Example 1(b) above provided the product (15 g, 80%): m.p. 112°–114° C.

c) 2-[3-(4-Hydroxybutoxy)-4-methoxyphenyl]ethylamine. Using a solution of ethyl 4-[2-methoxy-4-(2-nitroethenyl)phenoxy]butanoate (7.74 g, 25 mmol) in an analogous method to that of Example 2 above provided an oil (3.82 g, 64%).

N-{2-[3-(4-Hydroxybutoxy)-4-methoxyphenyl]ethyl}oxamide. Using a solution of 2-[3-(4-hydroxybutoxy)-4-methoxyphenyl]ethylamine (3.35 g, 14.0 mmol) in an analogous method to that of Example 5(g) above provided the oxamide (2.1 g, 48%): m.p. 162°–163° C.

Analysis Calc. for $C_{15}H_{22}N_2O_5 \cdot \frac{1}{4} H_2O$: C 58.05, H 7.15, N 9.03; found: C 57.06, H 6.97, N 8.77.

EXAMPLE 8

N-[2-(3,4-Dimethoxyphenyl)ethyl]oxamide a) N-[2-(3,4-Dimethoxyphenyl)ethyl]oxamide. Using a solution of 2-(3,4-dimethoxyphenyl)ethylamine (703 mg, 4.0 mmol) in 1,2-dimethoxyethane in an analogous method to Example 5(g) above provided the oxamide (210 mg, 21%): m.p. 171°–172.5° C.

Analysis Calc. for $C_{12}H_{16}N_2O_4$: C 57.13, H 6.39, N 11.10; found: C 57.15, H 6.42, N 11.09.

EXAMPLE 9

N-[2-(3,4-Dimethoxyphenyl)ethyl]-N-hydroxyoxamide a) (3,4-Dimethoxyphenyl)acetaldehyde oxime. To a solution of 2-(3,4-dimethoxyphenyl)ethylamine (1.70 mL, 10.0 mmol) in methanol (10 mL) at 0° C. under an argon atmosphere was added sodium tungstate dihydrate (132 mg, 0.4 mmol), followed by the dropwise addition of 30% aqueous hydrogen peroxide (1.1 mL, 10.0 mmol). After 2 h at 0° C., the mixture was allowed to warm to room temperature. Stirring was continued for an additional 4 h, at which, time the mixture was recooled and additional sodium tungstate dihydrate (131 mg, 0.4 mmol) and 30% aqueous hydrogen peroxide (1.1 mL, 10.0 mmol) were added. The mixture was allowed to warm to room temperature and stirred overnight. The reaction was quenched by the addition of aqueous sodium bisulfite and concentrated under reduced pressure. The residue was dissolved in methylene chloride, washed successively with aqueous sodium bisulfite (2×) and water and dried (potassium carbonate). The solvent was removed in vacuo to provide an orange oil (1.75 g, 90%) which was used without further purification.

b) N-[2-(3,4-Dimethoxyphenyl)ethyl]-N-hydroxyamine. To a solution of (3,4-dimethoxyphenyl)acetaldehyde oxime (503 mg, 2.6 mmol) and methyl orange (catalytic amount) in methanol (3 mL) under an argon atmosphere was added sodium cyanoborohydride (108 mg, 1.7 mmol). Immediately following this addition, methanolic hydrogen chloride (10 mL) was added to maintain a reddish-brown color, and the reaction mixture was stirred at room temperature for 1 h. The solvent was removed in vacuo and water was added to the residue. The solution was made basic by the addition of 15% sodium hydroxide and extracted with methylene chloride (3×). The combined organic extracts were dried (potassium carbonate) and the solvent was removed in vacuo to provide a yellow oil (451 mg, 89%).

c) N-[2-(3,4-Dimethoxyphenyl)ethyl]-N-hydroxamide. To a suspension of oxamic acid (195 mg, 2.21 mmol) in 1,2-dimethoxyethane (7 mL) under an argon atmosphere was added dropwise N-methylmorpholine (0.27 mL, 2.42 mmol), followed by ethyl chloroformate (0.23 mL, 2.42 mmol). After stirring for 1 h at room temperature, a solution of N-[2-(3,4-dimethoxyphenyl)ethyl]-N-hydroxyamine (417 mg, 2.10 mmol) in 1,2-dimethoxyethane (5 mL) was added, and the resulting mixture was stirred for 4 h. Saturated aqueous ammonium chloride was added, and the mixture was extracted with methylene chloride (2×). The combined organic extracts were washed successively with 10% hydrochloric acid and water and dried (potassium carbonate). The solvent was removed in vacuo and the residue was purified by flash chromatography, eluting with 5% methanol/methylene chloride, and recrystallized from methanol/methylene chloride to provide the oxamide (98 mg, 17%): m.p. 143°–144° C.

Analysis Calc. for $C_{12}H_{16}N_2O_5 \cdot \frac{2}{3} H_2O$: C 52.41, H 6.14, N 10.19; found: C 52.24, H 5.75, N 10.12.

EXAMPLE 10

N'-(6-t-Butyloxycarbonylaminohexyl)-N-[2-(3-cyclopentyloxy-4-methoxyphenyl)ethyl]oxamide a) N'-(6-t-Butyloxycarbonylaminohexyl)-N-[2-(3-cyclopenyloxy-4-methoxyphenyl)ethyl]oxamide. To a mixture of N-[2-(3-cyclopentyloxy-4-methoxyphenyl)ethyl]oxamic acid (750 mg, 2.44 mmol) in dimethylformamide (10 mL) under an argon atmosphere at −15° C. was added N-methylmorpholine (0.31 mL, 2.82 mmol) followed by isobutyl chloroformate (0.36 mL, 2.80 mmol). After stirring for 15 min, a solution of 1-(amino)-6-t-butyloxycarbonylamino)-hexane (790 mg, 3.65 mmol, prepared from the hydrochloride salt by treatment with saturated aqueous sodium carbonate and methylene chloride extraction) in 1:1 dimethylformamide/tetrahydrofuran (4 mL) was added, and the resulting mixture was stirred at room temperature for 4 h. The reaction mixture was partitioned between methylene chloride and dilute aqueous hydrochloric acid. The organic extract was washed with saturated aqueous sodium carbonate and dried (potassium carbonate). The solvent was removed in vacuo and the residue was purified by flash chromatography, eluting with ether to provide the oxamide (560 mg, 45%) as a solid. A portion of the product was recrystallized from methylene chloride/ether: m.p. 135°–137° C.

Analysis Calc. for $C_{27}H_{43}N_3O_6$: C 64.13, H 8.57, N 8.31; found: C 64.09, H 8.26, N 8.22.

EXAMPLE 11

N'-(6-Aminohexyl)-N-[2-(3-cyclopentyloxy-4-methoxyphenyl)ethyl]oxamide

N'-(6-Aminohexyl)-N-[2-(3-cyclopentyloxy-4-methoxyphenyl)ethyl]oxamide. A solution of N'-(6-t-butyloxycarbonylaminohexyl)-N-[2-(3-cyclopentyloxy-4-methoxyphenyl)ethyl]oxamide (480 mg, 0.95 mmol) in methylene chloride (5 mL) and trifluoroacetic acid (5 mL) was stirred at room temperature for 1 hour. The reaction mixture was concentrated under reduced pressure and the residue was partitioned between methylene chloride and saturated aqueous sodium carbonate. The organic extract was dried (potassium carbonate) and the solvent was removed under reduced pressure. The residue was dissolved in methylene chloride and concentrated. Ether and hexanes were added and the mixture was filtered. The filtrate was allowed to stand and the solid which formed was collected by filtration to provide a cream-colored powder (241 mg, 63%): m.p. 105°–110° C.

Analysis Calc. for $C_{22}H_{35}N_3O_4 \cdot \frac{1}{2} H_2O$: C 63.74, H 8.75, N 10.14; found: C 63.70, H 8.24, N 9.69.

EXAMPLE 12

N-[2-(3-Cyclopentyloxy-4-methoxyphenyl)ethyl]-N'-(4-nitrobenzyl)oxamide a) N-[2-(3-Cyclopentyloxy-4-methoxyphenyl)ethyl]-N'-(4-nitrobenzyl)oxamide. To a solution of 2-(3-cyclopenyloxy-4-methoxyphenyl)ethyloxamic acid (231 mg, 0.75 mmol) in methylene chloride (10 mL) under an argon atmosphere was added 1-(3-dimethylaminopropyl)-3-ethylcarbodiimide hydrochloride (180 mg, 0.94 mmol), followed by 4-dimethylaminopyridine (231 mg, 1.89 mmol) and p-nitrobenzylamine hydrochloride (178 mg, 0.94 mmol). The reaction mixture was stirred at room temperature overnight, then partitioned between methylene chloride and water. The organic extract was dried (magnesium-sulfate) and the solvent was removed under reduced pressure. The residue was purifed by flash chromatography, eluting with 9:1 ether/methylene chloirde to provide a solid (230 mg, 69%), which was recrystallized from ether/methylene chloride: m.p. 148°–150° C.

Analysis: Calc. for C23H27N3O6: C 62.57, H 6.16, N 9.52; found: C 62.72, H 6.39, N 9.72.

EXAMPLE 13

N'-(4-Acetamidobenzyl)-N-[2-(3-cyclopentyloxy-4-methoxyphenyl)ethyl]oxamide a) N'-(4-Aminobenzyl)-N-[2-(3-cyclopentyloxy-4-methoxyphenyl)ethyl]oxamide. To a solution of N'-[2-(3-cyclopentyloxy-4-methoxyphenyl)ethyl]-N-(4-nitrobenzyl)oxamide (200 mg, 0.45 mmol) in 4:5 methanol/tetrahydrofuran (18 mL) under an argon atmosphere was added ammonium formate (395 mg, 6.27 mmol) and 10% palladium on activated carbon (50 mg). The resulting mixture was stirred at room temperature for 3 h, then diluted with methylene chloride and filtered through a pad of Celite. The solvent was removed under reduced pressure and the residue was partitioned between methylene chloride and water. The organic extract was dried (sodium sulfate) and the solvent was removed in vacuo to provide a white solid (170 mg, 91%), which was used without further purification.

b) N'-(4-Acetamidobenzyl)-N-[2-(3-cyclopentyloxy-4-methoxyphenyl)ethyl]oxamide. To a solution of N'-(4-aminobenzyl)-N-[2-(3-cyclopentyloxy-4-methoxyphenyl)ethyl]-oxamide (170 mg, 0.41 mmol) in methylene chloride (10 mL) under an argon atmosphere was added pyridine (0.15 mL, 1.85 mmol) and acetic anhydride (0.15 mL, 1.59 mmol). The resulting mixture was stirred at room temperature overnight, then poured into chloroform and washed with dilute aqueous hydrochloric acid and dried (sodium sulfate). The solvent was removed in vacuo and the residue was recrystallized from methanol/chloroform to provide a white solid (116 mg, 62%): m.p. 217°-218° C.

Analysis Calc. for C25H31N3O5.¼ H2O: C 65.56, H 6.93, N 9.17; found: C 65.35, H 6.88, N 9.27.

EXAMPLE 14

N'-(4-Acetamidobenzyl)-N-[2-(3-cyclopentyloxy-4-methoxyphenyl)ethyl]oxamide

Using a solution of 2-(3-cyclopentyloxy-4-methoxyphenyl)ethyloxamic acid (231 mg, 0.75 mmol) in an analogous method to that of Example 12 above except using 4-acetamidoaniline (142 mg, 0.95 mmol) and only 1 equivalent of 4-dimethylamino pyridine (DMAP) provided the title compound. m.p. 235°-236° C.

Analysis Calc. for C24H29N3O5.¼ H2O: C 65.59, H 6.65, N 9.56; found: C 64:79, H 6.61, N 9.58.

EXAMPLE 15

N-[2-(3-Cyclopentyloxy-4-methoxyphenyl)ethyl]oxamide

To a suspension of oxamic acid (1.76 g, 20 mmol) in 1,2-dimethoxyethane (75 mL) under an argon atmosphere was added dropwise N-methylmorpholine (2.55 mL, 23 mmol) followed by ethyl chloroformate (2.20 mL, 23 mmol). After stirring for 1 h at room temperature, a solution of 2-(3-cyclopentyloxy-4-methoxyphenyl)ethylamine (4.65 g, 20 mmol) in 1,2-dimethoxyethane (30 mL) was added over 5 min, and the resulting mixture was stirred for 2 h. Saturated aqueous ammonium chloride was added and the solvent was removed under reduced pressure. The solid residue was dissolved in methanol/methylene chloride, washed successively with water, 10% hydrochloric acid, aqueous sodium bicarbonate and water and dried (potassium carbonate). The solvent was removed in vacuo and the residue was purified by flash chromatography, eluting with 1% i-propanol/methylene chloride to provide the oxamide (1.82 g, 30%): m.p. 175°-175.5° C.

Analysis Calc. for C16H22N2O4: C 62.73, H 7.24, N 9.14; found: C 62.61, H 7.32, N 8.98.

EXAMPLE 16

N-[2-(3-Cyclopentyloxy-4-methoxyphenyl)ethyl]-N'-hydroxyoxamide

To a solution of N-[2-(3-cyclopentyloxy-4-methoxyphenyl)ethyl]oxamic acid (651 mg, 2.12 mmol) in methylene chloride (5 mL) containing 2 drops of dimethylformamide at 0° C. under an argon atmosphere was added oxalyl chloride (0.39 mL, 4.45 mmol) and the resulting mixture was stirred for 1 h. This was added to a solution of hydroxylamine hydrochloride (591 mg, 8.50 mmol) and triethylamine (1.75 mL, 12.70 mmol) in 1:5 water/tetrahydrofuran (10 mL) at 0° C. under an argon atmosphere. The reaction mixture was stirred at 0° C. for 1 hour then allowed to warm to room temperature and stirred an additional 2 h. The mixture was partitioned between water and methylene chloride and the organic extract was dried (potassium carbonate). The solvent was removed in vacuo and the residue was purified by flash chromatography, eluting with 1:5:94 acetic acid/methanol/methylene chloride, to provide the hydroxy oxamide (489 mg, 72%): m.p. 136°-137° C.

Analysis Calc. for C16H22N2O5: C 59.62, H 6.88, N 8.69; found: C 59.60, H 7.18, N 8.63.

EXAMPLE 17

N-[2-(3-Cyclopentyloxy-4-methoxyphenyl)ethyl]-N-hydroxyoxamide (a) (3-Cyclopentyloxy-4-methoxy)phenylacetaldehyde oxime. Using a solution of 2-(3-cyclopentyloxy-4-methoxy-phenyl)ethylamine (1.017 g, 4.3 mmol) in an analogous method to that of Example 9(a) above provided the oxime (978 mg, 90%), which was used without further purification.

(b) N-[2-(3-Cyclopentyloxy-4-methoxyphenyl)ethyl]-N-hydroxyoxamine. Using a solution of (3-cyclopentyloxy-4-methoxy)phenylacetaldehyde oxime (971 mg, 3.9 mmol) in an analogous method to that of Example 9(b) above provided the hydroxyamine (144 mg, 15%).

(c) N-[2-(3-Cyclopentyloxy-4-methoxyphenyl)ethyl]-N-hydroxyoxamide. Using a solution of N-[2-(3-cyclopentyloxy-4-methoxyphenyl)-ethyl]-N-hydroxyoxamine (144 mg, 0.6 mmol) in an analogous method to that of Example 9(c) above provided the title oxamide (36 mg, 19%): m.p. 98°-99° C.

Analysis Calc. for C16H22N2O5: C 59.62, H 6.88, N 8.69; found: C 59.64, H 6.87, N 8.55.

EXAMPLE 18

N'-Amino-N-[2-(3-cyclopentyloxy-4-methoxyphenyl)ethyl]oxamide

Using a solution of N-[2-(3-cyclopentyloxy-4-methoxyphenyl)ethyl]oxamic acid (301 mg, 0.98 mmol) in an analogous method to Example 10 above except using 1,2-dimethoxyethane (3 mL) instead of DMF as a solvent, an anhydrous hydrazine (37 mL, 1.18 mmol) instead of 1-(amino) 6-t-butyloxycarbonylamino)hexane provided the amino oxamide (48 mg, 15%): m.p. 121°-122° C.

Analysis Calc. for C16H23N3O4: C 59.80, H 7.21, N 13.08; found: C 59.41, H 7.31, N 12.83.

EXAMPLE 19

N-(4-Acetylaminobenzyl)-N-[2-(3-cyclopentyloxy-4-methoxyphenyl)ethyl]oxamide (a) N-(4-Acetylaminobenzyl)-N-[2-(3-cyclopentyloxy-4-methoxyphenyl)ethyl]oxamine. A mixture of 4-(acetylamino)-benzaldehyde (555 mg, 3.40 mmol) and 2-(3-cyclopentyloxy-4-methoxyphenyl)ethylamine (801 mg, 3.40 mmol) in toluene (10 mL) was refluxed for 24 h with azeotropic removal of water. The solvent was then removed under reduced pressure. To the residue, which was dissolved in tetrahydrofuran (2 mL), was added ether saturated with hydrogen chloride (2 mL). After 5 min, the solvent was removed under reduced pressure. To the residue, which was dissolved in methanol (7 mL), was added dropwise a solution of sodium cyanoborohydride (213 mg, 3.38 mmol) in methanol (2 mL). After stirring at room temperature for 2.5 h, aqueous sodium bicarbonate was added to the reaction mixture, which was then concentrated under reduced pressure. The residue was partitioned between methylene chloride and aqueous sodium bicarbonate and the organic extract was dried (potassium carbonate). Removal of the solvent in vacuo and purification of the residue by flash chromatography, eluting with 3% methanol/methylene chloride, provided a viscous yellow oil (1.144 g, 88%).

(b) N-(4-Acetylaminobenzyl)-N-[2-(3-cyclopentyloxy-4-methoxyphenyl)ethyl]oxamide. Using a solution of N-(4-acetylaminobenzyl)-N-[2-(3-cyclopentyloxy-4-methoxyphenyl)ethyl]amine (1.14 g, 2.98 mmol) in an analogous method of Example 5(g) above provided the title oxamide yielding (234 mg, 17%): m.p. 117°–120° C.

Analysis Calc. for $C_{25}H_{31}N_3O_5 \cdot \frac{1}{8} H_2O$: C 65.88, H 6.91, N 9.22; found: C 65.80, H 6.95, N 9.15.

EXAMPLE 20

N-[2-(3-cyclopentyloxy-4-methoxyphenyl)propyl]oxamide (a) α-Bromo-3-cyclopentyloxy-4-methoxytoluene. To 3-cyclopentyloxy-4-methoxybenzaldehyde (5.0 g, 22.7 mmol) was added lithium bromide (3.94 g, 45.4 mmol) and acetonitrile (25 mL). Upon dissolution, the reaction mixture was cooled to 0° C. Trimethylsilylchloride (4.32 mL, 34.0 mmol) was slowly added and the reaction mixture was allowed to warm to room temperature and stirred for 15 min. The reaction mixture was again cooled to 0° C. and 1,1,3,3-tetramethyldisiloxane (6.68 mL, 34.0 mmol) was added dropwise. The resulting mixture was allowed to warm to room temperature. After stirring for 2 h, the mixture was separated into two layers. The lower layer was removed, diluted with methylene chloride and filtered. The filtrate was concentrated under reduced pressure, dissolved in methylene chloride and filtered. The solvent was removed in vacuo to provide a light tan oil (6.6 g, 100%) which was used without further purification.

(b) (3-Cyclopentyloxy-4-methoxyphenyl)acetonitrile. To a solution of α-bromo-3-cyclopentyloxy-4-methoxytoluene (6.6 g, 23.0 mmol) in dimethylformamide (10 mL) under an argon atmosphere was added a suspension of powdered sodium cyanide (2.5 g, 51.0 mmol) in dimethylformamide (40 mL). The resulting mixture was stirred at room temperature for 24 h, then poured into cold water (250 mL) and extracted three times with ether/ethyl acetate. The combined organic extracts were washed three times with water and dried (sodium sulfate). The solvent was removed in vacuo and the residue was purified by flash chromatography, eluting with 30% ethyl acetate/hexanes to provide a pale yellow oil (4.45 g, 84%).

(c) 2-(3-Cyclopentyloxy-4-methoxyphenyl)propionitrile. To a solution of diisopropylamine (0.61 mL, 4.3 mmol) in dry tetrahydrofuran (6 mL) under an argon atmosphere at 0° C. was added dropwise n-butyl lithium in hexanes (2.5M, 1.73 mL, 4.33 mmol). After stirring at 0° C. for 30 min, this mixture was cooled to −78° C. and a solution of 3-(cyclopentyloxy-4-methoxyphenyl)acetonitrile (1.0 g, 4.32 mmol) in dry tetrahydrofuran (3 mL) was added in a steady stream. After 6 min, this solution was added via canula to a solution of iodomethane (0.64 g, 4.5 mmol) in tetrahydrofuran (5 mL) under an argon atmosphere at −78° C. The mixture was allowed to warm to room temperature and stirred overnight. The solvent was removed in vacuo and the residue partitioned between ether and dilute aqueous hydrochloric acid. The ether layer was washed twice with dilute aqueous hydrochloric acid, once with water, once with dilute aqueous sodium bicarbonate and dried (sodium sulfate). After solvent evaporation, the residue was purified by flash chromatography, eluting with 2:1 hexanes/ether to provide a colorless oil (0.5 g, 47%).

(d) 2-(3-Cyclopentyloxy-4-methoxyphenyl)propylamine. To a solution of (3-cyclopentyloxy-4-methoxyphenyl)propionitrile (0.5 g, 2.0 mmol) in methanol (15 mL) was added 70% perchloric acid (0.32 g, 2.2 mmol) and 10% palladium on activated carbon (92 mg). The resulting mixture was hydrogenated at 50 psi hydrogen for 2 h and filtered through a pad of Celite. The filtrate was concentrated in vacuo. The residue was partitioned between methylene chloride and aqueous sodium carbonate and the methylene chloride layer was washed three times with water and dried (potassium carbonate). Solvent removal provided an oil (0.5 g, 100%).

(e) N-[2-(3-Cyclopentyloxy-4-methoxyphenyl)propyl]-oxamide. To a suspension of oxamic acid (0.27 g, 3 mmol) in 1,2-dimethoxyethane (10 mL) under an argon atmosphere was added dropwise N-methylmorpholine (0.36 mL, 3.3 mmol) followed by isobutyl chloroformate (0.43 mL, 3.3 mmol). After stirring for 1.5 h at room temperature, a solution of 2-(3-cyclopentyloxy-4-methoxyphenyl)propylamine (0.5 g, 2 mmol) in 1,2-dimethoxyethane (5 mL) was added and the resulting mixture was stirred overnight. The solvent was removed under reduced pressure. The solid residue was dissolved in chloroform, washed successively with dilute hydrochloric acid and water and dried (sodium sulfate). The solvent was removed in vacuo and the residue was purified by flash chromatography, eluting with 10% ether/chloroform. A second flash chromatography elution with 50% ethyl acetate/chloroform provided the oxamide (0.14 g, 22%): m.p. 175°–176.5° C.

Analysis Calc. for $C_{17}H_{24}N_2O_4$: C 63.73, H 7.55, N 8.74; found: C 63.80, H 7.69, N 8.65.

EXAMPLE 21

N-[2-(3-cyclopentyloxy-4-methoxyphenyl)-2-methylpropyl]oxamide (a) 2-(3-Cyclopentyloxy-4-methoxyphenyl)-2-methylpropionitrile. To a solution of diisopropylamine (1.7 mL, 12 mmol) in dry tetrahydrofuran (16 mL)

under an argon atmosphere at 0° C. was added dropwise n-butyl lithium in hexanes (2.5M, 4.9 mL, 12.3 mmol). After stirring at 0° C. for 30 min, this mixture was cooled to −78° C. and hexamethylphosphoramide (2.3 mL, 13.3 mmole) and a solution of 3-(cyclopentyloxy-4-methoxyphenyl)acetonitrile (1.0 g, 4.32 mmol) in dry tetrahydrofuran (3 mL) were added in sequence. After 30 min, the green solution was allowed to warm to −20° C. and iodomethane (3.3 g, 23.2 mmol) was added dropwise, The mixture was allowed to warm to room temperature and stirred overnight. The solvent was removed in vacuo and the residue partitioned between ether and dilute aqueous hydrochloric acid. The ether layer was washed twice with dilute aqueous hydrochloric acid, once with water and dried (sodium sulfate). Solvent evaporation provided a colorless oil (1.2 g) which was used without purification.

(b) 2-(3-cyclopentyloxy-4-methoxyphenyl)-2-methyl-proplyamine. To a solution of (3-cyclopentyloxy)-4-methoxyphenyl)-2-methylpropionitrile (0.9 g, 3.5 mmol) in methanol (50 mL) was added Raney nickel (50% slurry in water, 5 mL, washed three times with water and then three times with methanol prior to use) and concentrated ammonium hydroxide (1.5 mL). The resulting mixture was hydrogenated at 52 psi hydrogen for 1 h and filtered through a pad of Celite. The filtrate was concentrated in vacuo. The residue was partitioned between methylene chloride and aqueous sodium carbonate and the methylene chloride layer was dried (potassium carbonate). Solvent removal provided an oil (0.9 g, 98%).

(c) N-[2-(3-Cyclopentyloxy-4-methoxyphenyl)-2-methylpropyl]oxamide. The title compound was produced in an analogous method to Example 20, part (e) above (0.27 g, 24%): m.p. 108°–109.5° C.

Analysis Calc. for $C_{18}H_{26}N_2O_4$: C 64.65, H 7.84, N 8.38; found: C 64.60, H 7.91 N 8.33.

EXAMPLE 22

N-[2-(3-Cyclopentyloxy-4methylthiophenyl)ethyl]oxamide (a) 3-Cyclopentyloxy-4-methylthiobenzaldehyde. To a solution of 3-cyclopentyloxy-4-nitrobenzaldehyde (4.00 g, 17.0 mmol) in dimethylformamide (23 mL) under an argon atmosphere was added sodium thiomethoxide (132 g, 18.7 mmol). The resulting mixture was stirred for 30 min, then poured into water and extracted four times with ether. The combined organic extracts were washed twice with water and saturated aqueous sodium chloride and dried (sodium sulfate). The solvent was removed in vacuo. The residue was purified by flash chromatography, eluting with a solvent gradient of 15–50% ethyl acetate/hexanes to provide the thioether (1.72 g, 43%) as an orange oil.

(b) 3-Cyclopentyloxy-4-methylthio-β-nitrostyrene. Using a solution of 3-cyclopentyloxy-4-methylthiobenzaldehyde (1.70 g, 7.2 mmol) in the analogous method of Example 1(b) provided the nitrostyrene yielding (1.51 g, 75%): m.p. 121°–122° C.

(c) 2-[3-Cyclopentyloxy-4-methylthiophenyl]ethylamine. Using a solution of 3-cyclopentyloxy-4-methylthio-β-nitrostyrene (1.50 g, 5.4 mmol) in the analogous method of Example 2 above provided the amine (1.08 g, 80%).

(d) N-[2-(3-Cyclopentyloxy-4-methylthiolphenyl)ethyl]oxamide. Using a solution of 2-[3-cyclopentyloxy-4-methylthiophenyl]ethylamine (379 mg, 1.5 mmol) in the analogous method of Example 5(g) above provided the oxamide yielding (102 mg, 21%): m.p. 174°–175° C.

Analysis Calc. for $C_{16}H_{22}N_2O_3S$: C 59.60, H 6.88, N 8.69, S 9.94; found C 59.29, H 6.75, N 8.48, S 9.79.

EXAMPLE 23

N-[2-(3-Cyclopentyloxy-4-methylsulfoxylphenyl)ethyl]oxamide

To a solution of sodium periodate (97 mg, 0.5 mmol) in water at 0° C. under an argon atmosphere was added a suspension of N-[2-(3-cyclopentyloxy-4-methylthiophenyl)ethyl]oxamide (132 mg, 0.4 mmol) in methanol (4 mL). After workup the title sulfone compound was produced. (145 mg, 80%): m.p. 166°–167° C.

Analysis Calc. for $C_{16}H_{22}N_2O_4S \cdot 0.21H_2O$: C 56.16, H 6.60, N 8.19, S 9.37; found C 56.17, H 6.53, N 8.12, S 9.20.

EXAMPLE 24

N-[2-(3-Cyclopentyloxy-4-methylsulfonylphenyl)ethyl]oxamide

To a suspension of N-[2-(3-cyclopentyloxy-4-(methylthiophenyl)-ethyl]oxamide (50 mg, 0.16 mmol) in methylene chloride (2 mL) at 0° C. under an argon atmosphere was added m-chloroperoxybenzoic acid (79 mg, 0.46 mmol). After stirring for 45 min, the mixture was poured into methylene chloride and washed successively with aqueous sodium bisulfate, water, aqueous sodium bicarbonate and saturated aqueous sodium chloride and dried (potassium carbonate). The solvent was removed in vacuo and the residue was purified by flash chromatography, eluting with 2% methanol/methylene chloride to provide the sulfone (53 mg, 94%): m.p. 185°–186.5° C.

Analysis Calc. for $C_{16}H_{22}N_2O_5S \cdot 0.15H_2O$: C 53.80, H 6.29, N 7.86, S 8.98; found C 53.80, H 6.31, N 7.79, S 8.70.

EXAMPLE 25

Ethyl 2-(3-cyclopentyloxy-4-methoxyphenyl)-3-oxamidopropionate (a) Ethyl (3-cyclopentyloxy-4-methoxyphenyl)cyanoacetate. To a suspension of sodium hydride (1.32 g of 80% suspension in mineral oil, 44.0 mmol) in toluene (60 mL) under an argon atmosphere was added a solution of diethyl carbonate (3.47 g, 29.4 mmol) and (3-cyclopentyloxy-4-methoxyphenyl)acetonitrile (3.36 g, 14.5 mmol) in toluene (5 mL). The resulting mixture was heated at reflux for 1 hour with azeotropic removal of ethanol. The reaction mixture was allowed to cool to room temperature and stirred overnight. The mixture was partitioned between ice water and ether. The organic phase was extracted with aqueous sodium hydroxide. The aqueous phase was acidified with dilute aqueous hydrochloric acid and extracted with ether. The ether extract was dried (sodium sulfate) and the solvent was removed in vacuo. The residue was recrystallized from water/methanol to provide the product (2.97 g, 68%).

(b) Ethyl 3-amino-2-(3-cyclopentyloxy-4-methoxyphenyl)propionate.

To a solution of ethyl (3-cyclopentyloxy-4-methoxyphenyl)cyanoacetate (0.65 g, 2.14 mmol) in absolute ethanol (100 mL) was added 70% perchloric acid (0.14 mL, 2.36 mmol) and 10% palladium on carbon (0.19 g).

The resulting mixture was hydrogenated at 50 psi hydrogen for 2.5 h and filtered through a pad of Celite. The filtrate was concentrated in vacuo. The solid residue was partitioned between methylene chloride and aqueous sodium carbonate and the organic layer was dried (potassium carbonate). Removal of the solvent in vacuo provided an oil (0.66 g, 100%).

(c) Ethyl 2-(3-cyclopentyloxy-4-methoxyphenyl)-3-oxamidopropionate.

Using a solution of ethyl 3-amino-2-(3-cyclopentyloxy-4-methoxyphenyl)propionate (0.66 g, 2.14 mmol) in the analogous method of Example 5(g) above provided the title compound yielding (0.13 g, 16%): m.p. 184°–184.5° C.

Analysis Calc. for $C_{19}H_{26}N_2O_6$: C 60.30, H 6.93, N 7.40; found: C 60.70, H 6.89, N 7.64.

EXAMPLE 26

Methyl 2-(3-cyclopentyloxy-4-methoxyphenyl)-3-oxamidopropionate (a) Methyl (3-cyclopentyloxy-4-methoxyphenyl)cyanoacetate.

Using a suspension of (3-cyclopentyloxy-4-methoxyphenyl)acetonitrile (8.6 g, 37.2 mmol) in an analogous method to that of Example 25(a) above except using dimethyl carbonate instead of diethyl carbonate provided the title compound yielding a solid (7.45 g, 69%).

(b) Methyl 3-Amino-2-(3-cyclopentyloxy-4-methoxyphenyl)propionate.

Using a solution of methyl (3-cyclopentyloxy-4-methoxyphenyl)cyanoacetate (2.5 g, 8.6 mmol) in an analogous method to that of Example 25(b) above provided the titlte compound as an oil (2.5 g, 100%).

(c) Methyl 2-(3-cyclopentyloxy-4-methoxyphenyl)-3-oxmidopropionate.

Using a isobutyl chloroformate (1.9 mL, 14.8 mmol) and a solution of methyl 3-amino-2-(3-cyclopentyloxy-4-methoxyphenyl)-propionate (2.5 g, 8.6 mmol) in an analogous method to that of Example 5(g) above provided the oxamide: m.p. 182.5°–183° C.

Analysis Calc. for $C_{18}H_{24}N_2O_6$: C 59.33, H 6.64, N 7.69; found: C 59.29, H 6.60, N 7.61.

EXAMPLE 27

N-[2-(3,4-Didifluoromethoxyphenyl)ethyl]oxamide a) Methyl N-[2-(3,4-dibenzyloxyphenyl)ethyl]oxamate A solution of 3,4-dibenzyloxyphenethylamine hydrochloride (5 g, 13.5 mmol) in methylene chloride (50 mL) was cooled to 0° C. and treated with triethylamine (4.15 mL, 29.7 mmol) and methyl oxalyl chloride (1.37 mL, 14.9 mmol). The reaction was stirred at room temperature under an argon atmosphere for 2 h, then partitioned between acidic water and methylene chloride. The extract was was washed with dilute sodium bicarbonate, dried (magnesium sulfate) and evaporated. Purification by trituration with ether and hexane provided a tan solid (5.2 g, 92%): m. p. 84° C.

b) N-[2-(3,4-Dibenzyloxyphenyl)ethyl]oxamide

A suspension of methyl N-[2-(3,4-dibenzyloxyphenyl)ethyl]oxamate (5.0 g, 11.9 mmol) in methanol (100 mL) contained in a Fischer-Porter pressure vessel under argon was cooled to −78° C. Ammonia (ca. 60 mL) was condensed into the vessel, the vessel was sealed and allowed to come to room temperature. The suspension was allowed to stir at room temperature under a pressure of approximately 60 psi for 17 h. The mixture was cooled to −78° C., the vessel was opened and the vigorously stirred suspension was allowed to come to room temperature under a stream of argon. After 1.5 h, the solvent was removed in vacuo and the solid was triturated with 20% methylene chloride/ether to provide a white solid (4.5 g, 93%): m.p. 187° C.

c) N-[(2-(3,4-Dihydroxyphenyl)ethyl]oxamide To a solution of N-[2-(3,4-dibenzyloxyphenyl)ethyl]oxamide (4.0 g, 9.89 mmol) in methanol (120 mL) and dimethylformamide (40 mL) was added 10% palladium on carbon (1.0 g). The resulting mixture was hydrogenated at 55 psi for 4 h and filtered through a pad of celite. The filtrate was concentrated in vacuo to provide a light grey solid (2.2 g, 100%). m.p. >210° C.

d) N-[(2-(3,4-Bis-difluoromethoxyphenyl)ethyl]oxamide A suspension of N-[2-(3,4-dihydroxyphenyl)ethyl]oxamide (336 mg, 1.5 mmol) and anhydrous potassium carbonate (829 mg, 6 mmol) in dimethylformamide (4 mL) contained in a stainless steel bomb under an argon atmosphere was cooled to −78° C. Chlorodifluoromethane (ca. 2 mL) was condensed into the vessel, the vessel was sealed, allowed to come to room temperature and then heated at 80°–90° C. for 7 h. The mixture was cooled to −78° C., the vessel was opened and the vigorously stirred suspension was allowed to come to room temperature under a stream of argon. After 1 h, the mixture was partitioned between methylene chloride/isopropanol and acidic water and The organic extract was dried (sodium sulfate) and evaporated to a white solid. Purification by flash chromatography, eluting with 10% isopropanol/chloroform, followed by trituration of the resultant solid with methylene chloride/hexane, provided a white solid (120 mg, 25%): m.p. 153°–155° C.

Analysis Calc. for C12H12F4N2O4.1/10 H2O: C 44.21, H 3.77, N 8.59; found: C 44.54, H 3.57, N 8.64.

EXAMPLE 28

N-[(3,4-Diethoxyphenyl)ethyl]oxamide

A suspension of N-[(3,4-dihydroxyphenyl)ethyl]oxamide (280 mg, 1.25 mmol), anhydrous potassium carbonate (363 mg, 2.6 mmol) and iodoethane (0.22 mL, 2.75 mmol) in dimethylformamide (3 mL) under an argon atmosphere was heated at 70° C. After 4 h, additional iodoethane (0.1 mL) was added and the mixture was heated for an additional hour. The mixture was cooled to room temperature and partitioned between methylene chloride and acidic water. The organic extract was dried (magnesium sulfate) and evaporated. Purification by flash chromatography, eluting with 3% methanol/chloroform, followed by trituration of the resultant solid with ether, provided a tan solid (99 mg, 28%): m.p. 168°–169° C.

Analysis Calc. for C14H20N2O4: C 59.99, H 7.19, N9.99; found: C 59.88, H 7.19, N 9.94.

EXAMPLE 29

N-[2-Cyano-2-(3-cyclopentyloxy-4-methoxyphenyl)ethyl]oxamide a) 2-Cyano-2-(3-cyclopentyloxy-4-methoxyphenyl)acetamide A solution of methyl 2-cyano-2-(3-cyclopentyloxy-4-methoxyphenyl)acetate (2.1 g, 7.26 mmol), produced by the method of Example 26(a), in concentrated ammonium hydroxide (50 mL) was stirred at room temperature for four days. A thick white precipitate formed after the first half hour. The reaction was cooled to 0° C., acidified to pH 2–3 with 10% aqueous hydrochloric acid, extracted three times with methylene chloride/methanol and dried (magnesium sulfate). The solvent was removed in vacuo to provide an off-white solid (1.75 g, 88%): m.p. 160°–162° C.

b) 3-(t-Butoxycarbonylamino)-2-(3-cyclopentyloxy-4-methoxyphenyl)propioamide To a solution of 2-cyano-2-(3-cyclopentyloxy-4-methoxyphenyl)acetamide (504 mg, 1.85 mmol) in methanol (25 mL) was added 70% perchloric acid (179 µL, 1.9 mmol) and 10% palladium on carbon (30 mg). The resulting mixture was hydrogenated at 50 psi for 2 h and filtered through a pad of celite. The filtrate was concentrated in vacuo. The solid residue was partitioned between methylene chloride and aqueous sodium carbonate and the organic layer was dried (sodium sulfate). The solvent was removed in vacuo, and the residue was dissolved in methylene chloride (25 mL) and treated with di-t-butyl-dicarbonate (0.5 mL, 2.18 mmol). After 20 h, the solvent was evaporated and the residue was purified by flash chromatography, eluting with 1:1 ethyl acetate/hexanes, to provide a pale yellow solid (331 mg, 47.4%).

c) 3-(t-Butoxycarbonylamino)-2-(3-cyclopentyloxy-4-methoxyphenyl)propionitrile A solution of 3-(t-butoxycarbonylamino)-2-(3-cyclopentyloxy-4-methoxyphenyl)propioamide (285 mg, 0.75 mmol) in dry tetrahydrofuran (5 mL) was treated with pyridine (135 µL, 1.66 mmol) and with trifluoroacetic anhydride (120 µL, 0.83 mmol) dropwise. The reaction was stirred at room temperature for 1.5 h, then quenched with ice and partitioned between methylene chloride and water. The organic extract was dried (magnesium sulfate) and concentrated. Purification by flash chromatography, eluting with 3:7 ethyl acetate/hexanes, provided an orange-yellow oil (262 mg, 97%).

d) 3-Amino-2-(3-cyclopentyloxy-4-methoxyphenyl)-propionitrile A solution of 3-(t-butoxycarbonylamino)-2-(3-cyclopentyloxy-4-methoxyphenyl)propionitrile (256 mg, 0.71 mmol) in methylene chloride (5 mL) cooled to 0° C. was treated with the dropwise addition of trifluoroacetic acid (1.0 mL) and stirred under argon for 2 h at 0° C. and 2 h at room temperature. The reaction was neutralized with solid sodium bicarbonate, diluted with methylene chloride and washed with aqueous sodium bicarbonate and then with water. The organic extract was dried (potassium carbonate) and evaporated to provide a yellow oil (178 mg, 97%).

e) Methyl N-[2-cyano-2-(3-cyclopentyloxy-4-methoxyphenyl)ethyl]oxamate A solution of 3-amino-2-(3-cyclopentyloxy-4-methoxyphenyl)propionitrile (356 mg, 1.37 mmol) in methylene chloride (8 mL) was cooled to 0° C. and treated with triethylamine (0.2 mL, 1.51 mmol) and methyl oxalyl chloride (0.14 mL, 1.51 mmol). The reaction was stirred under an argon atmosphere for 0.5 h, then partitioned between water and methylene chloride. The extract was dried (sodium sulfate) and evaporated. Purification by flash chromatography, eluting with 3:7 ethyl acetate/hexanes, provided a white foam (332 mg, 70%).

f) N-[2-cyano-2-(3-cyclopentyloxy-4-methoxyphenyl)phenyl]oxamate (332 mg, 0.96 mmol) in methanol (3 mL) was treated with lithium hydroxide monohydrate (126 mg, 2.88 mmol) and stirred for 5 min. The solvent was removed in vacuo, the resin acidified with 10% aqueous hydrochloric acid and partitioned between methylene chloride and water and extracted. The organic extract was dried (magnesium sulfate) and evaporated. The residue was dissolved in ethylene gylcol dimethyl ether (5 mL) and treated with N-methyl-morpholine (127 mL, 1.15 mmol) and isobutylchloroformate (143 mL, 1.1 mmol). After 10 min, the reaction was cooled to 0° C. and a solution of ammonia-saturated ethylene glycol dimethyl ether (5–10 mL) was added. The reaction was allowed to stir for 0.5 h at 0° C. and for 2 h at room temperature. The mixture was partitioned between methylene chloride/methanol and water and washed with 10% aqueous hydrochloric acid and water. The organic extract was dried (magnesium sulfate) and evaporated to a white solid. Purification by flash chromatography, eluting with 1:1 ethyl acetate/hexanes, provided a white solid which was triturated with ether, filtered and dried (106.2 mg, 33%): m.p. 176°–177° C.

Analysis Calc. for $C_{19}H_{21}N_3O_4$: C 60.96, H 6.44, N 12.54; found: C 61.35, H 6.81, N 11.86.

EXAMPLE 30

N-[1-Methyl-2-(3-cyclopentyloxy-4-methoxyphenyl)ethyl]oxamide a) 3-cyclopentyloxy-4-methoxyphenyl)ethyl]-β-nitro styrene A solution of 3-cyclopentyloxy-4-methoxyphenylbenzaldehyde (3.3 g, 15 mmol) in glacial acetic acid (25 mL) was treated with nitroethane (4.2 mL, 58.5 mmol) and ammonium acetate (1.65 g, 21.4 mmol) and heated at reflux under an argon atmosphere for 6 h. The solvent was removed in vacuo and the residue was partitioned between methylene chloride and 5% sodium bicarbonate. The organic layer was dried (potassium carbonate) and evaporated. Purification by flash chromatography, eluting with 7:3 chloroform/hexanes, provides an oil which is crystallied from hexanes (1.05 g, 25.3%).

b) N-[2-(3-Cyclopentyloxy-4-methoxyphenyl)ethyl]-methylamine Using a solution of the nitrosyrene (1.0 g, 3.61 mmol) from part (a) above in an analogous method to that of Example 2 above, provided title compound yielding (692 mg, 77%).

c) N-[1-Methyl-2-(3-cyclopentyloxy-4-methoxyphenyl)ethyl]oxamide Using a solution of N-[2-(3-cyclopentyloxy-4-methoxyphenyl)ethyl]methylamine (690 mg, 2.77 mmol) in ethylene glycol dimethyl ether in an analogous method to that of Example 5(g) provided the title compound yielding (333 mg, 38%): m.p. 197°–198° C.

Analysis Calc. for $C_{17}H_{24}N_2O_4 \cdot \frac{1}{2}H_2O$: C 61.99, H 7.65, N 8.50; found: C, H, N.

EXAMPLE 31

N-[2-Cyano-2-methyl-2-(3-cyclopentyloxy-4-methoxyphenyl)ethyl]oxamide a) 2-Cyano-2-(3-cyclopentyloxy-4-methoxyphenyl)-propionamide A solution of diisopropyl amine (525 µL, 6.5 mmol) in tetrahydrofuran (15 mL) at 0° C. was treated with the slow addition of n-butyllithium (2.5M, 1.4 mL) in hexanes and stirred under an argon atmosphere for 0.5 h. The reaction mixture was cooled to −78° C., and solid 2-cyano-2-(3-cyclopentyloxy-4-methoxyphenyl)acetamide (849 mg, 3.11 mmol) was added. After stirring for 0.5 h, methyl iodide (4.0 mL, 62 mmol) was added, and the reaction was stirred with warming to room temperature. After 1.5 h, the reaction mixture was partitioned between ether and water and was washed with 1.0M hydrochloric acid, water and the organic extracts dried (sodium sulfate). The concentrated crude product was purified by flash chromatography, eluting with 3:7 ethyl acetate/hexanes, to provide a white solid (466 rag, 52%).

b) 3-(t-Butoxycarbonylamino)-2-(3-cyclopentyloxy-4-methoxyphenyl)-2-methylpropioamide To a solution of 2-cyano-2-(3-cyclopentyloxy-4-methoxyphenyl)-propioamide (464 mg, 1.61 mmol) in methanol (25 mL) was added 70% perchloric acid (175 µL, 1.9 mmol) and 10% palladium on carbon (40 mg). The resulting mixture was hydrogenated at 50 psi for 2 h and filtered through a pad of celite. The filtrate was concentrated in vacuo. The solid residue was partitioned between methylene chloride and aqueous sodium carbonate and the organic layer was dried (sodium sulfate). The solvent was removed in vacuo, and the residue dissolved in methylene chloride (5 mL) and treated with di-t-butyl-dicarbonate (0.5 mL, 2.17 mmol). After 2 h, the solvent was evaporated and the residue was purified by flash chromatography, eluting with 4:6 ethyl acetate/hexanes, to provide the product (487 mg, 77%).

c) 3-(t-Butoxycarbonylamino)-2-(3-cyclopentyloxy-4-methoxyphenyl)-2-methylpropionitrile A solution of 3-(t-butoxycarbonylamino)-2-(3-cyclopentyloxy-4-methoxyphenyl)-2-methylpropioamide (487 mg, 1.24 mmol) in dry tetrahydrofuran (7 mL) at 0° C., was treated with pyridine (220 µL, 2.74 mmol) and with trifluoroacetic anhydride (195 µL, 1.36 mmol) dropwise. The reaction was stirred at room temperature for 3 h under an argon atmosphere, then quenched with ice and partitioned between methylene chloride and water. The organic extract was dried (magnesium sulfate) and concentrated to a residue which was purified by flash chromatography, eluting with 25:75 ethyl acetate/hexanes, to provide a white solid (402 mg, 87%).

d) 2-Amino-2-(3-cyclopentyloxy-4-methoxyphenyl)-propionitrile A solution of 3-(t-butoxycarbonylamino)-3-cyclopentyloxy-4-methoxyphenyl)-2-methylpropionitrile (400 mg, 1.07 mmol) in methylene chloride (5 mL) cooled to 0° C. was treated with the dropwise addition of trifluoroacetic acid (1.35 mL) and stirred under argon for 1.5 h at 0° C. and 2.5 h at room temperature. The reaction was neutralized with solid sodium bicarbonate, diluted with methylene chloride and washed with water. The organic extract was dried (potassium carbonate) and evaporated to provide the product (289 mg, 100%).

e) Methyl N-[2-cyano-2-methyl-2-(3-cyclopentyloxy-4-methoxyphenyl)ethyl]oxamate A solution of 3-amino-2-(3-cyclopentyloxy-4-methoxyphenyl)-2-methylpropionitrile (288 mg, 1.05 mmol) in methylene chloride (5 mL) was cooled to 0° C. and treated with triethylamine (0.13 mL, 1.16 mmol) and methyl oxalyl chloride (0.11 mL, 1.2 mmol). The reaction was stirred under an argon atmosphere for 0.5 h, then partitioned between water and methylene chloride. The extract was dried (sodium sulfate) and evaporated. Purification by flash chromatography, eluting with 1:1 ethyl acetate/hexanes, provided a white foam (315 mg, 83%).

f) N-[2-Cyano-2-methyl-2-(3-cyclopentyloxy-4-methoxyphenyl)ethyl]oxamide A solution of Methyl N-[2-cyano-2-methyl-2-(3-cyclopentyloxy-4-methoxyphenyl)ethyl]oxamate (312 mg, 0.87 mmol) in methanol (7 mL) was treated with lithium hydroxide monohydrate (110 mg, 2.6 mmol) and stirred for 0.5 h. The pH was adjusted to pH 2 with 10% aqueous hydrochloric acid and the solvent was removed in vacuo. The resin was partitioned between methylene chloride and water, extracted and the organic extract was dried (magnesium sulfate) and evaporated. The residue was dissolved in ethylene glycol dimethyl ether (5 mL) and treated with N-methylmorpholine (115 mL, 1.04 mmol) and isobutylchloroformate (130 mL, 1.0 mmol). After 10 min, the reaction was cooled to 0° C. and to the reaction an ammonia saturated ethylene glycol dimethyl ether solution (5–10 mL) was added. The reaction was allowed to stir for 0.5 h at 0° C. and for 2 h at room temperature and partitioned between methylene chloride/methanol and water and washed with 10% aqueous hydrochloric acid and water. The organic extract was died (magnesium sulfate) and evaporated to provided a white solid which was triturated with ether, filtered and dried (84 mg, 28%): m.p. 171°–172° C.

Analysis Calc. for $C_{18}H_{23}N_3O_4$: C 62.19, H 6.74, N 12.09; found: C 61.99, H 6.60, N 11.81.

EXAMPLE 32

N-[2-(3-Cyclopentyloxy-4-methoxyphenyl)ethyl]-N'-(4-pyridinylmethyl)oxamide

Using a solution of N-[2-(3-cyclopentyloxy-4-methoxyphenyl)ethyl]oxamic acid (284 mg, 0.92 mmol), EDAC (220 mg, 1.16 mmol) and dimethylaminopyridine (140, 1.25 mmol) and 4-aminomethyl pyridine in an analogous method to that of Example 12 above provided the title compound yielding (126 mg, 34%): m.p. 129°–131° C.

Analysis Calc. for $C_{17}H_{24}N_2O_4$.: C 63.73, H 7.55, N 8.74; found: C 63.36, H 7.23, N 8.65.

EXAMPLE 33

N-[2-(3-Cyclopentyloxy-4-methoxyphenyl)ethyl]-N'-(3-pyridinylmethyl)oxamide

Using a solution of N-[2-(3-cyclopentyloxy-4-methoxyphenyl)ethyl]oxamic acid (306 mg, 1.0 mmol) in ethylene glycol dimethyl ether (6 mL) was treated with N-methylmorpholine (130 µL, 1.2 mmol) and isobutyl chloroformate (147 µL, 1.15 mmol) in an anaglous method to that of Example 10 above with (3-Aminomethyl)-pyridine provided the product (42 mg, 11%): m.p. 148–149° C.

Analysis Calc. for $C_{22}H_{27}N_3O_4$: C 66.48, H 6.85, N 10.57; found: C 66.11, H 6.84, N 10.40.

EXAMPLE 34

N-[2-(3-Cyclopentyloxy-4-methoxyphenyl)ethyl]-N'-(4-pyridinyl)oxamide

The title compound was produced in an analogous manner to that of Example 10 and 33 above except using 4-Aminopyridine yielded (45 mg, 12%): m.p. 182° C.

Analysis Calc. for $C_{21}H_{25}N_3O_4$: C 65.78, H 6.57, N 10.96; found: C 65.47, H 6.53, N 10.93.

EXAMPLE 35

N-[2-(3-Cyclopentyloxy-4-methoxyphenyl)ethyl]-N'-(3-pyridinyl)oxamide

The title compound was produced in an analogous manner to that of Example 10 and 33 above except using 3-Aminopyridine yielded (226 mg, 59%): m.p. 167° C.

Analysis Calc. for $C_{21}H_{25}N_3O_4$: C 65.78, H 6.57, N 10.96; found: C 65.83, H 6.46, N 10.91.

EXAMPLE 36

N-[2-(3-Cyclopentyloxy-4-methoxyphenyl)ethyl]-N'-(2-pyridinylmethyl)oxamide

The title compound was produced in an analogous manner to that of Example 10 and 33 above except using (2-Aminomethyl)pyridine yielded (241 mg, 63%): m.p. 141°–143° C.

Analysis Calc. for $C_{22}H_{27}N_3O_4$: C 66.48, H 6.85, N 10.57; found: C 66.46, H 6.86, N 10.57.

EXAMPLE 37

N-[2-(3-Cyclopentyloxy-4-methoxyphenyl)ethyl]-N-methyloxamide a) N-[(t-Butoxycarbonyl)-3-(3-cyclopentyloxy-4-methoxyphenyl)ethyl]amine A solution of (3-cyclopentyloxy-4-methoxyphenyl)ethylamine (2.5 g, 10.62 mmol) in methylene chloride (25 mL) was treated with butyloxycarbonylanhydride (2.5 mL, 11.0 mmol) and stirred under an argon atmosphere for 2 h. The solvent was removed in vacuo and the residue was purified by flash chromatography. The product was eluted with 1:1 ether/hexanes as a colorless oil (3.04 g, 85%).

b) N-[Methyl-1-(t-butoxycarbonyl)-3-(3-cyclopentyloxy-4-methoxyphenyl)ethyl]amine A solution of N-[(t-butoxycarbonyl)-3-(3-cyclopentyloxy-4-methoxyphenyl)ethyl]amine (1.2 g, 3.6 mmol) in dimethylformamide (10 mL) was treated with sodium hydride (120 mg, 4.0 mmol of an 80% dispersion) and stirred at room temperature under an argon atmophere for 2 h. Methyl iodide (300 μL, 4.8 mmol) was added, and stirring continued for another 3 h. The solvent was removed in vacuo and the residue was partitioned between methylene chloride and acidic water. The organic layer was dried (potassium carbonate) and evaporated. Purification by flash chromatography, eluting with 3:1 hexanes/ether, provided the product (680 mg, 54%).

c) N-[1-Methyl-2-(3-cyclopentyloxy-4-methoxyphenyl)ethyl]amine Using a solution of N-[methyl-1-(t-butoxycarbonyl)-3-(3-cyclopentyloxy-4-methoxyphenyl)ethyl]amine (650 mg, 1.86 mmol) in the analogous method of Example 11 above provided the title compound as an oil (440 mg, 95%).

d) N-[2-(3-Cyclopentyloxy-4-methoxyphenyl)ethyl]-N-methyloxamide Using a solution of N-[1-methyl-2-(3-cyclopentyloxy-4-methoxyphenyl)ethyl]amine (300 mg, 1.2 mmol) in an analogous method of Example 5(g) above provided the title compound yielding (230 mg, 60%).

Analysis Calc. for $C_{17}H_{24}N_2O_4 \cdot \frac{1}{2} H_2O$: C 61.99, H 7.65, N 8.50; found: C 62.16, H 7.53, N 8.45.

EXAMPLE 38

N-[2-(3-Cyclopentyloxy-4-methoxyphenyl)ethyl]-N,N',N'-(trimethyl)oxamide a) N-[2-(3-Cyclopentyloxy-4-methoxyphenyl)ethyl]-N',N'-(dimethyl)oxamide using a solution of N-[2-(3-cyclopentyloxy-4-methoxyphenyl)ethyl]oxamic acid (300 mg, 0.98 mmol) in ethylene glycol dimethylether in an analogous method of Example 10 provided the title compound as an oil (220 mg, 68%).

b) N-[2-(3-Cyclopentyloxy-4-methoxyphenyl)ethyl]-N,N',N'-(trimethyl)oxamide A solution of N-[2-(3-cyclopentyloxy-4-methoxyphenyl)ethyl]-N',N'-(dimethyl)oxamide (220 mg, 0.66 mmol), in dimethylformamide (7 mL) was treated with sodium hydride (33 mg, 0.99 mmol of an 80% dispersion), 15-crown-5 ether (195 μL, 0.99 mmol) and stirred at 50° C. under an argon atmosphere for 1 h. In a separate flask, methyl iodide (327 μL, 5.3 mmol) was added to tetrahydrofuran (20 mL), and the anion solution was added to it. Stirring continued for another 18 h under an argon atmosphere. The solvent was removed in vacuo and the residue was partitioned between ethyl acetate and water and washed with water 5 times. The organic layer was dried (potassium carbonate) and evaporated. Purification by flash chromatography, eluting with 97:3 chloroform/methanol, provided an oil.

Analysis Calc. for $C_{19}H_{28}N_2O_4$: C 65.49, H 8.10, N 8.04; found: C 63.47, H 7.38, N 7.56.

EXAMPLE 39

N-[3-Hydroxy-2-(3-cyclopentyloxy-4-methoxyphenyl)-propyl]oxamide

N-[3-Hydroxy-2-(3-cyclopentyloxy-4-methoxyphenyl)propyl]oxamide A suspension of sodium borohydride (104 mg, 2.7 mmol) in ethylene glycol dimethyl ether (16 mL) under an argon atmosphere was treated with lithium chloride (121 mg, 2.8 mmol) and was stirred for 0.5 h. To it was added N-2-(3-cyclopentyloxy-4-methyloxyphenyl)ethyl-2-methoxycarbonyloxamide (100 mg, 0.27 mmol) and the reaction was stirred at room temperature for 2.5 h. The solvent was removed in vacuo and water, hydrochloric acid to make acidic, and sodium carbonate were added and the mixture was extracted with chloroform. The product was concentrated and purified by flash chromatography. The product eluted with 2.5–7% methanol in chloroform and was triturated with ether to provide a white solid (9 mg, 9%): m.p. 176° C.

EXAMPLE 40

2-Carboxamido-N-[2-(3-cyclopentyloxy-4-methoxyphenyl)ethyl]oxamic acid

Methyl 2-Carboxamido-N-[2-(3-cyclopentyloxy-4-methoxyphenyl)ethyl]oxamate Using a solution of 3-amino-2-(3-cyclopentyloxy-4-methoxyphenyl)propionamide (100 mg, 0.47 mmol) in methylene chloride (8 mL) in the analogous method of Example 3 provided the title compound yielding (124 mg, 78%): m.p. 164°–165° C.

[2-Carboxamido-N-2-(3-cyclopentyloxy-4-methoxyphenyl)ethyl]oxamic acid Using a solution of 2-carboxamido-N-2-(3-cyclopentyloxy-4-methoxyphenyl)-ethyloxamic acid methyl ester (95 mg, 0.26 mmol) in methanol (8 mL) in an analogous method to Example 4 above provided the product an off-white powder (11 mg, 73%): m.p. 188°–190° C.

EXAMPLE 41

N-[2-(3-Cyclopentyloxy-4-methoxyphenyl)ethyl]-N-(4-acetaminophenyl)oxamide a) Ethyl 2-(3-cyclopentyloxy-4-methoxyphenyl)acetate A mixture of methyl methylsulfinylmethyl sulfide (2.0 mL, 19.1 mmol) and powdered sodium hydroxide (80 mg, 2.0 mmol) was stirred at 70°–75° C. under an argon atmosphere for 0.5 h, 3-cyclopentyloxy-4-methoxyphenylbenzaldehyde (2.0 g, 9.1 mmol) was added and the reaction was continued heating for 1.5 h. The reaction was diluted with methylene chloride and washed with 0.5M hydrochloric acid, water and the organic extract was dried (potassium carbonate) and evaporated. Purification by flash chromatography, eluting with 4:6 ethyl acetate/hexanes provided a solid (2.5 g, 85%). The solid was dissolved in ethanol (15 mL), treated with ethanol saturated with hydrochloric acid (1 mL) stirred at reflux for 2.5 h. The solvent was removed in vacuo and the residue was purified by flash chromatography. The product eluted with 95:5 ethyl acetate/hexanes as a yellow oil (1.58 g, 63%).

b) 2-(3-Cyclopentyloxy-4-methoxyphenyl)acetic acid
Using a solution of ethyl 2-(3-cyclopentyloxy-4-methoxyphenyl)acetate (1.5 g, 5.5 mmol) in the analogous method of Example 4 except heating 1 hour at about 65°–70° C. provided the product as a yellow oil (1.4 g, 99%).

c) 2-(3-Cyclopentyloxy-4-methoxyphenyl)-N-(4-nitrophenyl)acetamide Using a solution of 2-(3-cyclopentyloxy-4-methoxyphenyl)acetic acid (1.4 g, 5.4 mmol) in the analogous method to Example 12 provided the product as a yellow solid (884 mg, 44%): m.p. 129°–131° C.

d) 2-(3-Hydroxy-4-methoxyphenyl)-N-(4-nitrophenyl)ethylamine To a solution of borane (3.0 mL, 1.0M solution in tetrahydrofuran) was added 2-(3-cyclopentyloxy-4-methoxyphenyl)-N-(4-nitrophenyl)acetamide (255 mg, 0.69 mmol) and the mixture was stirred under an argon atmosphere for 15 min. To the reaction was added 6N hydrochloric acid (5 mL) and the reaction was stirred at 120° C. for 1 h in an open atmosphere. The solution was cooled to 0° C., was basified with solid potassium carbonate (6.2 g, 45 mmol) and water was added. The mixture was partitioned between methylene chloride and water, and the organic layer was dried (potassium carbonate) and evaporated to a yellow oil (202.7 mg, 70%).

e) 2-(3-Cyclopentyloxy-4-methoxyphenyl)-N-(4-nitrophenyl)ethylamine A solution of 2-(3-hydroxy-4-methoxyphenyl)-N-(4-nitrophenyl)ethylamine (201 mg, 0.7 mmol) in dimethylformamide (5 mL) was treated with cesium carbonate (456 mg, 1.4 mmol) and cyclopentyl bromide and was stirred at 55°–60° C. under an argon atmosphere for 4 h. The mixture was filtered and partitioned between methylene chloride and aqueous sodium bicarbonate. The organic layer was dried (potassium carbonate) and evaporated. Purification by flash chromatography, eluting with 2:8 ethyl acetate/hexanes, provided the product (227 mg, 91%).

f) 2-(3-Cyclopentyloxy-4-methoxyphenyl)-N-(4-aminophenyl)ethylamine Using a solution of 2-(3-cyclopentyoxy-4-methoxyphenyl)-N-(4-nitrophenyl)ethylamine (218 mg, 0.61 mmol) in the analogous method of Example 13 (a) provided the title compound as a purple oil (151 mg, 76%).

g) 2-(3-Cyclopentyloxy-4-methoxyphenyl)-N-(4-acetamidophenyl)ethylamine A solution of 2-(3-cyclopentyoxy-4-methoxyphenyl)-N-(4-aminophenyl)ethylamine (119 mg, 0.37 mmol) in methylene chloride (1 mL) was treated with pyridine (1 drop) and 10% acetic anhydride in methylene chloride (400 μL, 0.43 mmol). The reaction was stirred under an argon atmosphere for 1 h. The reaction was partitioned between methylene chloride and water, and the organic layer was dried (magnesium sulfate) and evaporated to provide the product (131 mg, 96%).

h) N-[2-(3-Cyclopentyloxy-4-methoxyphenyl)ethyl]-N-(4-acetaminophenyl)oxamide Using a solution of 2-(3-cyclopentyoxy-4-methoxyphenyl)-N-(4-acetamidophenyl)ethylamine (194 mg, 0.53 mmol) in the analogous method of Example 5(g) provided the title oxamide yielding a solid (7 mg, 3%).

Analysis Calc. for $C_{24}H_{29}N_3O_5 \cdot \frac{3}{8}H_2O$: C 63.45, H 6.80, N 9.25; found: C 63.06, H 6.35, N 9.66.

EXAMPLE 42

N-[2-oxo-2-(3-cyclopentyloxy-4-methoxyphenyl)ethyl]oxamide

N-[2-oxo-2-(3-cyclopentyloxy-4-methoxyphenyl)ethyl]oxamide A solution of pyridinium dichromite (236 mg, 0.63 mmol) in dimethylformamide (3.5 mL) under an argon atmosphere was treated with N-[2-hydroxy-2-(3-cyclopentyloxy-4-methoxyphenyl)ethyl]oxamide (130 mg, 0.42 mmol) and was stirred for 5 h. Ether (10 mL) was added, the mixture was stirred for an additional 0.5 h and then was filtered through florisil. The filtrate was concentrated and partitioned between ethyl acetate and water. The organic layer was washed three times with water and then dried (sodium sulfate). Purification by flash chromatography, eluting with 9:1 chloroform/methanol, provided a white solid, which was recrystallized from ether (40 mg, 29.7%).

Analysis Calc. for $C_{16}H_{20}N_2O_5 \cdot \frac{1}{8}H_2O$: C 58.35, H 6.43, N 8.51; found: C 58.89, H 6.12, N 8.07.

EXAMPLE 43

N-[2-hydroxy-2-(3-cyclopentyloxy-4-methoxyphenyl)ethyl]oxamide 2-(3-Cyclopentyloxy-4-methoxyphenyl)-2-hydroxyethane A solution of 3-cyclopentyloxy-4-methoxybenzaldehyde (7 g, 32 mmol) in tetrahydrofuran (100 mL) was cooled to −78° C. under argon and treated with methyl lithium (25 mL, 35.2 mmol) dropwise over five minutes. The reaction was stirred for 1.5 h while warming to room temperature. Water was added (1.15 ml, 64 mmol) and the solvent was removed in vacuo. The yellow solid was exposed to high vacuum for 10 minutes and used without further purification.

1-(3-Cyclopentyloxy-4-methoxyphenyl)-1-oxoethane A solution of 2-(3-cyclopentyloxy-4-methoxyphenyl)-2-hydroxyethane (7.08 g, 32 mmol) in methylene chloride (150 mL) was treated with pyridinium dichromate (16.8 g, 44.7 mmol) and the mixture was stirred under argon for 4.5 h. Ether (800 mL) was added and the mixture was stirred for 0.5 h. The reaction was filtered through florisil and washed well with ether. The solvent was removed in vacuo to provide an orange oil. Purification by flash chromatography, eluting with 97:3 methylene chloride/ethyl acetate, provided an off-white solid (3.0 g, 40%).

1-(3-Cyclopentyloxy-4-methoxyphenyl)-1-oxo-2-bromoethane In a flask under argon was placed finely powdered copper (II) bromide (3.36 g, 16.2 mmol), which was dissolved in ethyl acetate (20 mL) and heated to reflux. A warm solution of 1-(3-cyclopentyloxy-4-methoxyphenyl)-1-oxo-2-bromoethane (2.0 g, 8.54 mmol) in chloroform (20 mL) was added with continued refluxing. After 2.5 h, evolution of hydrogen bromide had ceased and the reaction was allowed to cool to room temperature. The reaction was stirred for an additional 1.5 h and then filtered through a glass fiber filter to remove the lavender solid. The filtrate was concentrated and purification of the residue by flash chromatography, eluting with 8:2 hexanes/ether, provided a yellow solid (1.09 g, 41%). The solid was unstable and was stored under argon at −30° C.

1-(3-Cyclopentyloxy-4-methoxyphenyl)-1-oxo-2-azidoethane A solution of 1-(3-cyclopentyloxy-4-methoxyphenyl)-1-oxo-2-bromoethane (1.0 g, 3.19 mmol) in dimethyformamide (12 mL) was treated with sodium azide (208 mg, 3.19 mmol) and the reaction was heated at 72° C. for 1.75 h. The reaction was cooled, poured into water and extracted with ethyl acetate. The organic layer was washed with water and dried (sodium sulfate). The solvent was removed in vacuo and the orange solid was stored under argon at −30° C. (1.0 g, 100%).

1-(3-Cyclopentyloxy-4-methoxyphenyl)-2-azidoethanol A solution of 1-(3-cyclopentyloxy-4-methoxyphenyl)-1-oxo-2-azidoethane (840 mg, 3.1 mmol) in methanol (40 mL) under an argon atmosphere was cooled to 0° C. and treated with neat sodium borohydride (232 mg, 6.2 mmol). After stirring for 0.25 h, water (0.5 mL), 15% sodium hydroxide (0.5 mL) and then water (1 mL) were added. The mixture was filtered, concentrated, partitioned between methylene chloride and water, and extracted twice. The organic layer was dried (potassium carbonate) and evaporated to provide a colorless oil (700 mg, 81.4%). This oil in ether (20 mL) was added to a suspension of lithium aluminum hydride (227 mg, 6.3 mmol) in ether (20 mL) under an argon atmosphere. The reaction was stirred at room temperature for 2 h, then was treated with water (0.2 mL), 15% sodium hydroxide (0.2 mL), and water (0.6 mL). The mixture was then filtered, the filtrate was dried (sodium sulfate) and concentrated to provide a white solid (490 mg, 92.8%).

Methyl N-[2-hydroxy-2-(3-cyclopentyloxy-4-methoxyphenyl)ethyl]oxamate A solution of (490 mg, 1.95 mmol) in tetrahydrofuran (8 mL) was cooled to −78° C. and treated with triethylamine (0.3 mL, 2.15 mmol) and methyl oxalyl chloride (0.22 mL, 1.95 mmol). The reaction was stirred under an argon atmosphere for 1.5 h, then partitioned between water (pH ~2) and methylene chloride. The extract was dried (potassium carbonate) and evaporated to a white solid (550 mg, 83.6%).

N-[2-hydroxy-2-(3-cyclopentyloxy-4-methoxyphenyl)ethyl]oxamide A solution of methyl N-[2-hydroxy-2-(3-cyclopentyloxy-4-methoxyphenyl)phenyl]oxamate (550 mg, 1.63 mmol) in methanol (15 mL) was cooled to −78° C. and treated with liquid ammonia (15 mL). The reaction was allowed to warm to room temperature and stirred for 4 h. The ammonia was evaporated and chloroform was added (20 mL). The mixture was washed with water, dried (potassium carbonate) and evaporated. Purification by flash chromatography, eluting with 9:1 chloroform/methanol, provided a white solid (500 mg, 100%): m.p. 180°–181° C.

Analysis Calc. for $C_{16}H_{22}N_2O_5 \cdot \frac{1}{2}H_2O$: C 57.99, H 7.00, N 8.45; found: C 57.99, H 6.92, N 8.14.

Example 44

N-[2-(3-Difluoromethoxy-4-methoxyphenyl)ethyl]oxamide a) N-[2-(4-Difluoromethoxy-3-hydroxyphenyl)ethyl]oxamide and N-[2-(3-Difluoromethoxy-4-hydroxyphenyl)ethyl]oxamide A suspension of N-[2-(3,4-dihydroxyphenyl)ethyl]oxamide (1.0 g, 4.5 mmol) and anhydrous potassium carbonate (2.5 g, 18.1 mmol) in dimethylformamide (15 mL) contained in a glass pressure bomb under an argon atmosphere was cooled to −78° C. Chlorodifluoromethane (ca. 6 mL) was condensed into the vessel, the vessel was sealed and allowed to come to room temperature, and the mixture was stirred under pressure for 96 h. After cooling to −78° C., the vessel was opened and the vigorously stirred suspension was allowed to come to room temperature under a stream of argon. After 1 h, the mixture was partitioned between ethyl acetate and acidic water and the organic extract was dried (magnesium sulfate) and evaporated. Purification by two successive flash chromatographies, eluting with 10% ethyl acetate/ether, provided: N-[2-(4-difluoromethoxy-3-hydroxyphenyl)ethyl]oxamide as a glassy foam (65 mg, 5.3%), N-[2-(3-difluoromethoxy-4-hydroxyphenyl)ethyl]oxamide as a glassy foam (79 mg, 6.5%) and N-[2-(3,4-Bis-difluoromethoxyphenyl)ethyl]oxamide (48 mg, 3.3%).

b) N-[2-(3-Cyclopentyloxy-4-difluoromethoxyphenyl)ethyl]oxamide A mixture of N-[2-(4-difluoromethoxy-3-hydroxyphenyl)ethyl]oxamide (59 mg, 0.215 mmol), potassium carbonate (33 mg, 0.236 mmol) and bromocyclopentane (24 μL, 0.236 mmol) in dimethylformamide (3 mL) was heated under an argon atmosphere at 100° C. for 3 h. The mixture was allowed to cool and was partitioned between ethyl acetate and 5% aqueous sodium carbonate. The organic extract was washed with aqueous sodium carbonate and dried (potassium carbonate). The solvent was removed in vacuo and the residue was purified by flash chromatography, eluting with 10% ethyl acetate/ether, to provide a white solid (50 mg, 67%): m.p. 166°–169° C.

Analysis Calc. for $C_{16}H_{20}F_2N_2O_4 \cdot \frac{1}{4}H_2O$: C 55.41, H 5.96, N 8.08; found: C 55.63, H 5.81, N 8.05.

EXAMPLE 45

N-[2-(3-Cyclopentyloxy-4-difluoromethoxyphenyl)ethyl]oxamide

N-[2-(3-Difluoromethoxy-4-methoxyphenyl)ethyl]oxamide A mixture of N-[2-(3-difluoromethoxy-4-hydroxyphenyl)ethyl]oxamide (70 mg, 0.28 mmol), produced in Example 44, step (a) above, potassium carbonate (40 mg, 0.26 mmol) and bromocyclopentane (30 μL, 0.29 mmol) in dimethylformamide (2.5 mL) was heated under an argon atmosphere at 100° C. for 7 h. The mixture was allowed to cool, was partitioned between ethyl acetate and 5% aqueous sodium carbonate and the organic extract was dried (potassium carbonate). The solvent was removed in vacuo and the residue was purified by flash chromatography, eluting with 10% ethyl acetate/ether, to provide a white solid (34 mg, 46%): m.p. 164°–168° C.

Analysis Calc. for $C_{12}H_{14}F_2N_2O_4$: C 50.00, H 4.9, N 9.72; found: C 49.87, H 4.91, N 9.47.

EXAMPLE 46

Pivaloyloxymethyl N-[2-(3-cyclopentyloxy-4-methoxyphenyl)ethyl]oxamate

Pivaloxymethyl N-[2-(3-cyclopentyloxy-4-methoxyphenyl)ethyl]oxamate A solution of N-[2-(3-cyclopentyloxy-4-methoxyphenyl)ethyl]oxamic acid (125 mg, 0.41 mmol) in dimethylformamide (4 mL) was treated with triethylamine (79.5 μL, 0.56 mmol) and was stirred under an argon atmosphere for 0.75 h. The reaction was treated with chloromethylpivolate ( 117.3 μL, 0.82 mmol) and was stirred at room temperature for 18 h. The reaction was then heated to 70° C. for 1 h. The mixture was dissolved in ethyl acetate and washed four times with water. The organic extracts were washed twice with saturated sodium bicarbonate, dried (sodium sulfate), evaporated, and exposed to high vacuum for 18 h to provide a foam (150 mg, 85%).

Analysis Calc. for: $C_{22}H_{31}NO_7$: C: 62.69, H: 7.41, N: 3.32; found: C: 62.26, H: 7.52, N: 3.27.

EXAMPLE 47

(N,N-Dimethylaminocarbonylmethyl) N-[2-(3-cyclopentyloxy-4-methoxyphenyl)ethyl]oxamate (N,N-Dimethylaminocarbonylmethyl)-N-[2-(3-cyclopentyloxy-4-methoxyphenyl)ethyl]oxamate A solution of N-[2-(3-cyclopentyloxy-4-methoxyphenyl)ethyl]oxamic acid (125 mg, 0.41 mmol) in dimethylformamide (4 mL) was treated with triethylamine (62.4 μL, 0.45 mmol) and sodium iodide (6 mg, 0.04 mmol) and was stirred under an argon atmosphere for ten minutes. The reaction was treated with 2-chloro-N,N'-dimethylacetamide (79 μL, 0.45 mmol) and was heated to 100° C. for 5.5 h. The mixture was dissolved in ethyl acetate and washed four times with water. The organic extracts were dried (sodium sulfate), evaporated, and exposed to high vacuum for 18 h to provide an oil (80 mg, 50.1%).

Analysis: Calc. for: $C_{20}H_{28}N_2O_6 \cdot \frac{1}{3} H_2O$: C: 60.29, H: 7.25, N: 7.03; found: C: 60.29, H: 7.27, N: 6.96.

The following exemplified compounds may be prepared by analogous methods using the same techniques as those described above.

Example 48-N-[2-(3-Cyclopentyloxy-4-difluoromethoxyphenyl)ethyl]oxamide.
Example 49-N-[2,2-Dicyano-2-(3-cyclopentyloxy-4-methoxyphenyl)ethyl]oxamide.
Example 50-N-[2-Acetyleno-2-(3-cyclopentyloxy-4-methoxyphenyl)ethyl]oxamide.

The above description fully discloses the invention including preferred embodiments thereof. Modifications and improvements of the embodiments specifically disclosed herein are within the scope of the following claims. Without further elaboration, it is believed that one skilled in the art can, using the preceding description, utilize the present invention to its fullest extent. Therefore the Examples herein are to be construed as merely illustrative and not a limitation of the scope of the present invention in any way. The embodiments of the invention in which an exclusive property or privilege is claimed are defined as follows.

What is claimed is:

1. A compound which is:
   N-[2-(3-cyclopentyloxy-4-methoxyphenyl)ethyl]oxamide;
   N-[2-(3-cyclopentyloxy-4-methoxyphenyl)propyl]oxamide;
   N-[2-(3-cyclopentyloxy-4-methoxyphenyl)-2-methylpropyl]oxamide;
   N-[2-cyano-2-methyl-2-(3-cyclopentyloxy-4-methoxyphenyl)ethyl]oxamide;
   N-[2-(3-cyclopentyloxy-4-methoxyphenyl)ethyl]-N-methyloxamide;
   N-[2-(3-difluoromethoxy-4-methoxyphenyl)ethyl]oxamide;
   N-[2-(3-difluoromethoxy-4-methoxyphenyl)ethyl]oxamide; or
   N-[2-(3,4-didifluoromethoxyphenyl)ethyl]oxamide.

2. A pharmaceutical composition which comprises a compound according to claim 1 and a pharmaceutically acceptable carder or diluent.

3. A method of treating asthma or an allergic or inflammatory disease which comprises administering to a mammal in need thereof, an effective amount of a compound of claim 1.

* * * * *